United States Patent
Sato et al.

(10) Patent No.: US 10,349,627 B2
(45) Date of Patent: Jul. 16, 2019

(54) DETECTION DEVICE, RECOVERY METHOD THEREFOR AND MONITORING SYSTEM

(75) Inventors: Shigeru Sato, Morioka (JP); Hitoshi Mizuguchi, Shinjo (JP); Kazunori Ito, Shinjo (JP); Yasuo Okita, Shinjo (JP)

(73) Assignee: INCORPORATED NATIONAL UNIVERISTY IWATE UNIVERSITY, Iwate (JP)

(*) Notice: Subject to any disclaimer, the term of this patent is extended or adjusted under 35 U.S.C. 154(b) by 662 days.

(21) Appl. No.: 13/378,892

(22) PCT Filed: Jun. 17, 2010

(86) PCT No.: PCT/JP2010/060276
§ 371 (c)(1),
(2), (4) Date: Dec. 16, 2011

(87) PCT Pub. No.: WO2010/147175
PCT Pub. Date: Dec. 23, 2010

(65) Prior Publication Data
US 2012/0088988 A1    Apr. 12, 2012

(30) Foreign Application Priority Data
Jun. 19, 2009    (JP) .................................. 2009-146443

(51) Int. Cl.
*A61B 5/00*    (2006.01)
*A61B 5/07*    (2006.01)
(Continued)

(52) U.S. Cl.
CPC .......... *A01K 11/007* (2013.01); *A61B 5/0031* (2013.01); *A61B 5/073* (2013.01);
(Continued)

(58) Field of Classification Search
CPC .... A01K 11/007; A61B 5/14539; A61B 5/073
(Continued)

(56) References Cited

U.S. PATENT DOCUMENTS 2,799,274 A    7/1957    Eisenhut
4,002,547 A *  1/1977    Neti ..................... G01N 27/301
                                                                    204/296
(Continued)

FOREIGN PATENT DOCUMENTS

AT    505 607 A1    2/2009
JP    6-276877 A    10/1994
(Continued)

OTHER PUBLICATIONS

"Magnetic Susceptibility of the Elements and Inorganic Compounds", CRC Handbook of Chemistry and Physics 95th Edition (Internet Version 2015), Jan. 1, 2015, pp. 4-131-4-136.

*Primary Examiner* — Tiffany Weston
(74) *Attorney, Agent, or Firm* — Birch, Stewart, Kolasch & Birch, LLP

(57) ABSTRACT

A detection device is retained in the rumen of a cow by being orally administered to the cow, and detects the state of the inside of the rumen. The detection device wirelessly transmits measured values of the rumen pH as detection results. A monitoring unit (receiver and monitoring server) acquires information transmitted from the detection device, and monitors the state of the inside of the rumen. The detection device is configured to be recoverable orally from the rumen of the cow. The operating conditions of the detection device are recorded in the detection device ahead of time, and can be updated by means of a wireless signal transmitted from a setting unit to the detection device.

13 Claims, 18 Drawing Sheets

(51) Int. Cl.
  *A01K 11/00* (2006.01)
  *A61B 5/145* (2006.01)
(52) U.S. Cl.
  CPC ........ *A61B 5/14539* (2013.01); *A61B 5/4238* (2013.01); *A61B 5/6861* (2013.01); *A61B 2503/40* (2013.01)
(58) Field of Classification Search
  USPC .............................. 600/302, 549, 361, 101
  See application file for complete search history.

(56) References Cited

U.S. PATENT DOCUMENTS

| | | | | |
|---|---|---|---|---|
| 4,105,509 | A * | 8/1978 | Jungck | G01N 27/4035 204/414 |
| 5,697,384 | A * | 12/1997 | Miyawaki et al. | 128/899 |
| 5,984,875 | A | 11/1999 | Brune | |
| 6,468,408 | B2 * | 10/2002 | Thrier et al. | 204/435 |
| 6,694,161 | B2 * | 2/2004 | Mehrotra | A61B 5/0031 600/300 |
| 7,062,308 | B1 * | 6/2006 | Jackson | A61B 5/073 600/361 |
| 2003/0023150 | A1 * | 1/2003 | Yokoi et al. | 600/300 |
| 2003/0181788 | A1 | 9/2003 | Yokoi et al. | |
| 2004/0133089 | A1 * | 7/2004 | Kilcoyne et al. | 600/350 |
| 2004/0133131 | A1 * | 7/2004 | Kuhn | A01K 11/007 600/593 |
| 2004/0180391 | A1 * | 9/2004 | Gratzl | A61B 5/14528 435/14 |
| 2004/0260164 | A1 | 12/2004 | Kilcoyne et al. | |
| 2005/0034984 | A1 * | 2/2005 | Iwamoto et al. | 204/420 |
| 2008/0236500 | A1 | 10/2008 | Hodges et al. | |
| 2009/0048498 | A1 * | 2/2009 | Riskey | A61B 5/0031 600/302 |
| 2009/0182207 | A1 * | 7/2009 | Riskey et al. | 600/302 |

FOREIGN PATENT DOCUMENTS

| | | |
|---|---|---|
| JP | 9-294543 A | 11/1997 |
| JP | 2001-231460 A | 8/2001 |
| JP | 2003-530135 A | 10/2003 |
| JP | 2008-529631 A | 8/2008 |
| WO | WO-00/59376 A1 | 10/2000 |
| WO | WO 2006/085087 A2 | 8/2006 |

* cited by examiner

DETECTION DEVICE, RECOVERY METHOD THEREFOR AND MONITORING SYSTEM

TECHNICAL FIELD

The present invention relates to a detection device for detecting a state of a first stomach (rumen) of a ruminant, a method of recovering the device, and to a monitoring system. The present invention particularly relates to a detection device detecting the state of rumen while retained inside the rumen, a method of recovering the detection device from the ruminant, and a monitoring system for monitoring the state of rumen of the ruminant using the detection device.

BACKGROUND ART

With recent development of electronics, proposals of small-sized electronic devices intended to be placed in human or animal bodies have been made.

By way of example, National Patent Publication No. 2003-530135 (Patent Literature 1) discloses a monitoring device for monitoring at least one physiological parameter at an attachment site in a body. The monitoring device includes a detector for detecting the parameter, and a transmitter for transmitting data formed by the detector.

In the field of livestock raising or dairy husbandry, placement of an electronic device with a transmitter in the body of an animal and management or identification of individual sample using information from the electronic device have been proposed. By way of example, Japanese Patent Laying-Open No. 6-276877 (Patent Literature 2) discloses an in-vivo type individual piece identification equipment used retained in the rumen or a reticulum of a ruminant. The identification equipment includes a vessel formed of a material not eroded by gastric juice, an integrated circuit housed in the vessel, and an antenna provided inside or outside the vessel. The integrated circuit transmits data (identification code) stored in advance in response to electromagnetic waves generated outside the body of the animal, through a transmission antenna.

U.S. Pat. No. 5,984,875 (Patent Literature 3) discloses a sensor that senses a physiological parameter (such as temperature) of the ruminant and transmits the results of detection. The sensor has such a size and density that allows the sensor to be retained in the rumen or in the reticulum of the ruminant. Data transmitted from the sensor are received by an external receiver.

By way of example, National Patent Publication No. 2008-529631 (Patent Literature 4) discloses a sensing device configured to be easily swallowable by an animal. The sensing device includes a controller, a transmitter and an array of sensor elements. The transmitter is configured to transmit sensor data extracted from an array output.

CITATION LIST

Patent Literature

PTL 1: National Patent Publication No. 2003-530135
PTL 2: Japanese Patent Laying-Open No. 6-276877
PTL 3: U.S. Pat. No. 5,984,875
PTL 4: National Patent Publication No. 2008-529631

SUMMARY OF INVENTION

Technical Problem

For feeding management of milk cows and beef cattle, it is important to know the state of rumen. In order to know the state of rumen, typically, pH of the rumen liquid is measured.

Because of improved quality of feedstuff to milk cows, better technique of feeding management and developed breeding, lactation yield has been remarkably increased. In order to maintain high lactation yield, milk cows are fed with a large amount of condensed feedstuff. To enable higher lactation yield, however, feeding management ignoring physiology of cows has been spread widely. As a result, frequent occurrence of rumen acidosis and various metabolic diseases, infectious diseases, and hoof diseases related to rumen acidosis has been reported. Rumen acidosis and various related diseases are factors that hinder milk production.

The state in the cow rumen differs depending on the fed feedstuff and is closely related to occurrence of epidemic or to production of high quality milk. Rumen acidosis refers to a state where rumen pH decreased. The rumen pH decreases when a large amount of concentrated feedstuff is fed, or the order of feeding is inappropriate. Importance of measuring rumen pH comes to be widely recognized, and control of rumen acidosis utilizing rumen pH measurements comes to be a major problem for maintaining health of milk cows and satisfactory production of milk.

At present, however, technique for accurately measuring the state in the rumen has not been established. Specifically, in order to grasp the state in the rumen, rumen liquid must be taken from the cow. The rumen liquid sample may be taken orally using an oral catheter, or taken by puncture to the first stomach compartment using an injection needle. Oral sampling has a problem of saliva unavoidably mixed to the rumen liquid, and puncture to the stomach using an injection needle always has a possibility of bacterial infection. Therefore, accurate measurement of pH has been difficult.

Further, it is considered that temperature in the rumen increases as fermentation proceeds in the rumen. Therefore, in order to detect the state in the rumen, measurement of rumen temperature in addition to the measurement of rumen liquid pH is preferred. According to the conventional method, however, the temperature must be measured outside of the biological body. Thus, accurate measurement of rumen temperature has been impossible.

In addition, in order to take rumen liquid sample, it is necessary to restrain the cow, which is rather troublesome. This may leads to lower frequency of measurement of rumen liquid pH or temperature. Though detection of the state in the rumen is known to be an effective method of feeding management, it has not been a popular method, because of the reasons described above. As a result, many milk cows suffer from diseases related to rumen acidosis, resulting in the problem of lower production yield. Lower production yield is a serious problem for cattle farmers.

None of the references cited above specifically describes detection of the inner state of rumen of a ruminant (typically, cow), particularly, accurate detection of rumen pH.

Further, none of the references cited above specifically describes recovery of electronic equipment placed in a biological body. If, for instance, the electronic device cannot be taken out from a milk cow as long as she is alive, the same number of electronic devices as the number of milk cows must be provided. Such a situation increases the cost of monitoring system.

An object of the present invention is to provide a detection device capable of detecting the state of rumen of a ruminant, a method of recovering the detection device, and to provide a monitoring system including the detection device.

Solution to Problem

According to an aspect, the present invention provides a detection device for detecting internal state of a rumen of a ruminant, including a housing formed of a material having resistance to liquid component of contents in the rumen and having physical strength to withstand movement and inner pressure of the rumen, configured to enable oral administration to the ruminant and engageable with a recovery instrument orally inserted to the inside of the rumen. The housing has an opening for introducing the liquid component to a first chamber inside the housing. The detection device further includes a protection portion for sectioning the inside of the housing to the first chamber and a second chamber not permitting entrance of the liquid component, a measuring unit, a storage unit, a control unit, a communication unit and a battery. The measuring unit is placed in the first chamber of the housing for measuring a parameter related to the liquid component. The storage unit is placed in the second chamber of the housing for storing information related to operational conditions of the detection device. The control unit is placed in the second chamber of the housing for generating data related to the parameter from result of measurement by the measuring unit, based on the information stored in the storage unit. The communication unit is placed in the second chamber of the housing for transmitting through wireless communication the data related to the parameter generated by a process by the control unit. The battery is placed in the second chamber, for supplying electric power at least to the control unit and the communication unit.

Preferably, the recovery instrument is configured to be inserted to the inside of the rumen and to include a magnet used for taking out the detection device from the body of the ruminant. The housing includes a tapered portion tapered to be gradually narrower toward a front edge, and a coupling portion formed of at least one of ferromagnetic body and paramagnetic body. A portion defining the second chamber of the housing is configured to allow opening and sealing.

Preferably, the communication unit is configured to be capable of receiving through wireless communication new information for updating at least part of the operational conditions of the detection device. The control unit updates the information stored in the storage unit with the new information, when the new information is received by the communication unit.

Preferably, the information stored in the storage unit includes a unique number of the detection device, and transmission schedule of the data related to the parameter.

Preferably, the parameter includes a pH value of the liquid component. The measuring unit includes a pH sensor. The pH sensor includes a glass electrode, a gel containing internal solution, a comparison electrode at least partially arranged in the gel, a liquid junction formed of porous resin for controlling amount of liquid junction of the internal solution flowing out from the gel, and a temperature sensor for temperature compensation of pH measurement value of the liquid component by the glass electrode and the comparison electrode.

Preferably, the parameter includes a pH value of the liquid component. The measuring unit includes a pH sensor. The pH sensor includes a glass electrode, a potassium chloride saturated solution as an internal solution, a comparison electrode at least partially immersed in the potassium chloride saturated solution, a liquid junction formed of porous resin for controlling amount of liquid junction of the internal solution, and a temperature sensor for temperature compensation of pH measurement value of the liquid component by the glass electrode and the comparison electrode.

Preferably, the detection device further includes an amplifier circuit for amplifying an output of the pH sensor. The amplifier circuit includes a reference voltage setting unit for setting potential of the comparison electrode to a reference potential, and an amplifier for amplifying potential difference between potential of the glass electrode and the reference potential.

According to another aspect, the present invention provides a monitoring system including: the above-described detection device; a communication device configured to be capable of wireless communication with the detection device, for receiving the data transmitted through wireless communication from the detection device; and a monitoring device for collecting the data received by the communication device and for monitoring state of the rumen using the data.

Preferably, the communication unit of the detection device includes a first antenna for transmitting radio wave of transmission power of at most 10 mW. The communication device includes a second antenna for receiving the data through wireless communication. The second antenna has higher gain than the first antenna.

Preferably, the communication device is capable of receiving the data transmitted from each of a plurality of detection devices. The monitoring device collects data received by the communication device at least arranged at one location.

Preferably, the communication unit of the detection device is configured to be capable of receiving through wireless communication new information for updating at least part of the operational conditions of the detection device. The control unit updates the information stored in the storage unit with the new information, when the new information is received by the communication unit. The communication device includes a receiver for receiving the data transmitted through wireless communication from the detection device and a setting unit configured to be capable of transmitting through wireless communication the new information corresponding to each of the plurality of detection devices.

According to a still another aspect, the present invention provides a recovery method for recovering a detection device placed in a rumen of a ruminant for detecting inner state of the rumen. The detection device includes a housing formed of a material having resistance to liquid component of contents in the rumen and having physical strength to withstand movement and inner pressure of the rumen, configured to enable oral administration to the ruminant. The housing has a through hole formed to introduce the liquid component to a first chamber inside the housing. The detection device further includes a measuring unit placed in the first chamber of the housing for measuring a parameter related to the liquid component. The recovery method includes the steps of: inserting a recovery instrument having a portion engageable with the detection device retained in the body of the ruminant to the rumen; engaging the recovery instrument with the detection device; and recovering the recovery instrument and thereby taking out the detection device from the mouth of the ruminant.

Advantageous Effects of Invention

The present invention realizes the detection device capable of detecting the state of rumen of a ruminant, a method of recovering the detection device, and a monitoring system including the detection device.

DESCRIPTION OF EMBODIMENTS

Figure 1:
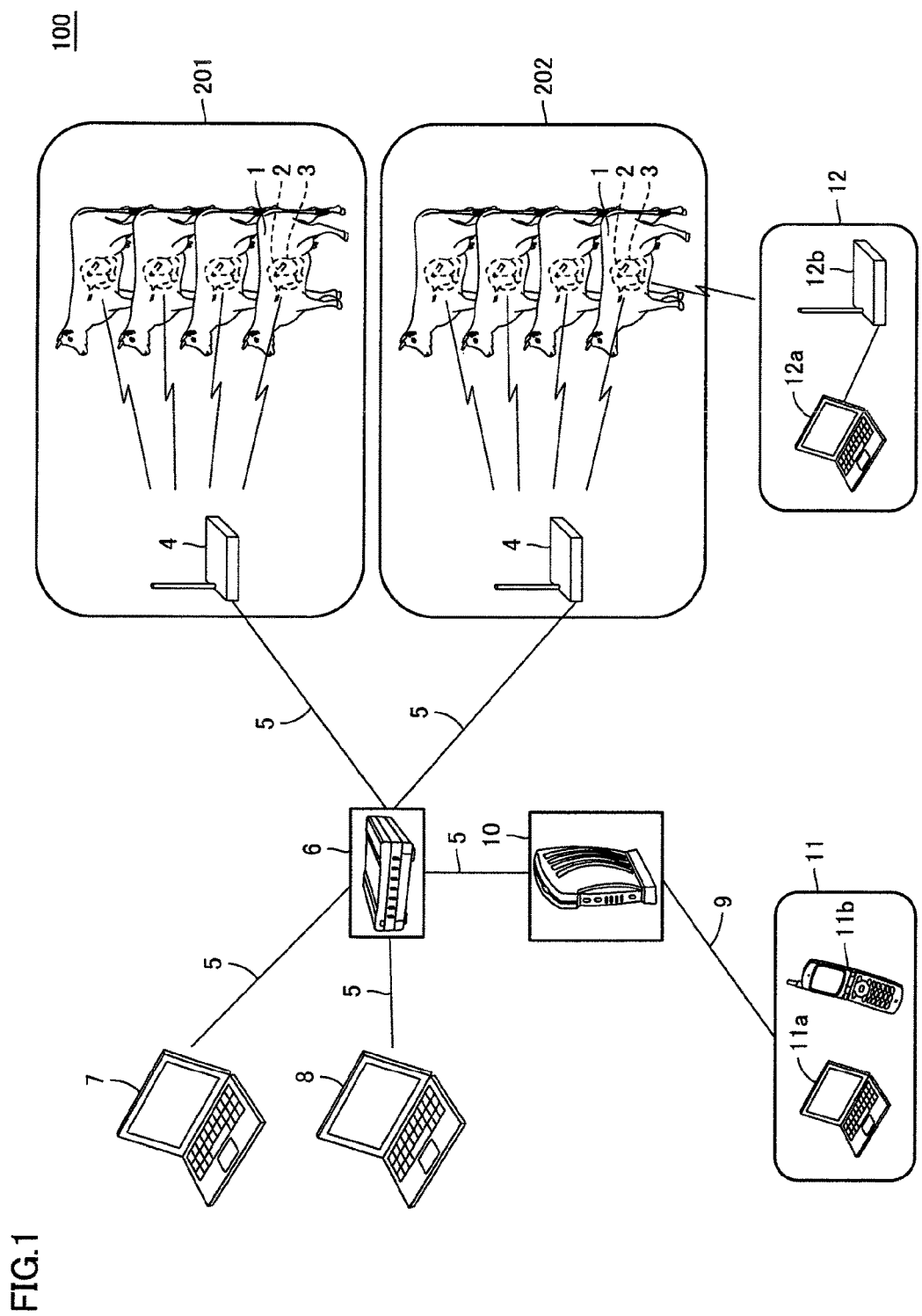
FIG. 1 schematically illustrates the overall configuration of a monitoring system 100 in accordance with a first embodiment of the present invention.

In the following, embodiments of the present invention will be described in detail with reference to the figures. In the figures, the same or corresponding portions are denoted by the same reference characters and description thereof will not be repeated.

Embodiment 1

FIG. 1 schematically illustrates the overall configuration of a monitoring system 100 in accordance with a first embodiment of the present invention. Referring to FIG. 1, monitoring system 100 in accordance with the first embodiment of the present invention collects pieces of information related to the state inside a rumen 3 of a cow 1, and monitors the state inside rumen 3 based on the information. The cow shown in FIG. 1 may be a milk cow or beef cattle. In the following description, it is assumed that cow 1 is a milk cow.

Monitoring system 100 includes a detection device 2 for detecting the state of rumen 3 of cow 1. Detection device 2 is placed in rumen 3 of cow 1, and detects the state inside rumen 3. Specifically, in order to detect the state in rumen 3, detection device 2 measures pH of rumen liquid.

The rumen liquid pH reflects the inner state of rumen 3. By way of example, if rumen pH lowers, it is highly likely that rumen acidosis occurs. Normally, the rumen pH is 7.0 to 6.0, and the state where rumen pH becomes 5.5 or lower is referred to as rumen acidosis. Rumen acidosis can be detected by measuring rumen pH.

Detection device 2 transmits data representing the results of measurement of rumen liquid pH together with a unique number allocated to detection device 2, through wireless communication. The unique number is stored in advance in detection device 2. Further, detection device 2 updates pieces of information related to operational conditions of detection device 2, in accordance with a wireless signal transmitted from outside the body of cow 1.

Detection device 2 is administered through the mouth of cow 1. Various known methods may be used for orally administering the detection device 2 and, therefore, detailed description thereof will not be repeated here.

Monitoring system 100 further includes a receiver 4 for receiving data transmitted through wireless communication from detection device 2, a LAN (Local Area Network) 5, a hub 6, a monitoring server 7, and a web server 8. At least receiver 4 and monitoring server 7 form a monitoring unit for monitoring the state inside the rumen of the cow.

Receiver 4 is configured to be able to receive data transmitted from each of a plurality of detection devices 2. The number of detection devices 2 connectable to one receiver 4 is not specifically limited. Therefore, as shown in FIG. 1, receiver 4 may be provided corresponding to each of the groups of cows 201 and 202. By way of example, cows 1 belonging to the groups 201 and 202 are each lactating dairy cow.

Receiver 4 is connected to each of monitoring server 7 and web server 8, through LAN 5 and hub 6. Based on the data transmitted from detection device 2, monitoring server 7 executes various processes for monitoring the state of rumen 3 of cow 1 to which detection device 2 has been administered. Further, receiver 4 is connectable to an external memory such as a USB (Universal Serial Bus) memory (not shown), and the received data may be transmitted to the external memory.

Monitoring server 7 periodically acquires measurement data from receiver 4. The period when monitoring server 7 acquires measurement data may be arbitrarily set. Monitoring server 7 has a database and registers the acquired data with the database.

Monitoring server 7 displays the data registered with the database in a prescribed format such as a table or a graph. The contents to be displayed may include the number for identifying an individual and time-change of pH value of the rumen corresponding to the number. Monitoring server 7 further has a function of monitoring the measurement data and a function of sending an electronic mail to an administrator of cow 1, such as the stock keeper or a veterinarian. For instance, if the measurement value of rumen pH of a certain cow decreases to 5.5 or lower, monitoring server 7 sends an electronic mail describing the identification number of the cow and information (such as current rumen pH value) to call attention of the administrator, to an address registered in advance.

Monitoring server 7 further stores various pieces of information related to management of cow 1, such as the time of feeding feedstuff, input by the user.

Web server 8 acquires the measurement data from the database of monitoring server 7, and displays the data on a browser in a prescribed format, such as a graph. Further, web server 8 has a user interface function and receives pieces of information for various operations of monitoring server 7 and receiver 4. Web server 8 transmits the input information to monitoring server 7, and in accordance with the information, monitoring server 7 executes various processes on itself or on receiver 4. Monitoring server 7 and web server 8 may be implemented, for example, by personal computers.

Monitoring system 100 further has a router 10 for connecting LAN 5 and WAN (Wide Area Network) 9 to each other. An information terminal 11 (in FIG. 1, a personal computer 11*a* and a portable terminal 11*b* are shown as examples) at a distant place is connected to WAN 9. Information terminal 11 displays the measurement data registered with the database of monitoring server 7 in a prescribed format (for example, a graph), and receives the electronic mail sent from monitoring server 7.

Monitoring system 100 further includes a setting unit 12. Setting unit 12 has a function of generating data related to setting of detection device 2, and a function of transmitting the data through wireless communication. Setting unit 12 includes a personal computer 12*a* as a data generating device, and a transmitter 12*b* for transmitting the data generated by personal computer 12*a* through wireless communication. It is noted, however, that setting unit 12 may be a portable device having the data generating device and the transmitter integrated.

Personal computer 12*a* generates unique number of detection device 2, operational conditions (for example, time interval for detection device to send data), instruction for calibrating detection device 2, and so on. Transmitter 12*b* transmits the data, instructions and the like generated by personal computer 12*a* through wireless communication. Receiving the information transmitted from transmitter 12*b* through wireless communication, detection device 2 updates the pieces of information that have been stored in advance with the information transmitted from transmitter 12*b*. It is noted that setting unit 12 can set operational conditions of detection device 2 and so on as needed, before and after the detection device 2 is administered to the cow 1.

Receiver 4 and setting unit 12 constitute a communication device capable of wireless communication with detection device 2.

In accordance with the first embodiment of the present invention, detection device 2 retained in rumen 3 detects the internal state of rumen 3. Therefore, the state inside the rumen can be grasped without taking rumen liquid. When pH of rumen liquid taken orally is measured, the nature of rumen liquid may highly likely be changed because of saliva mixed to the rumen liquid. Such a problem is avoided in the present embodiment and, therefore, pH value of rumen liquid can accurately be measured. Further, according to the first embodiment, detection device 2 transmits the result of detection, that is, measured value of rumen pH through wireless communication, and the monitoring unit (receiver 4 and monitoring server 7) acquires the information transmitted from detection device 2. Therefore, according to the present embodiment, it is possible to measure and monitor the state inside the rumen on a real-time basis for a long time.

Further, according to the first embodiment, detection device 2 is configured to be recoverable from rumen 3. Therefore, one detection device can be used repeatedly. Therefore, according to the first embodiment of the present invention, the cost for the monitoring system can be reduced.

Figure 2:
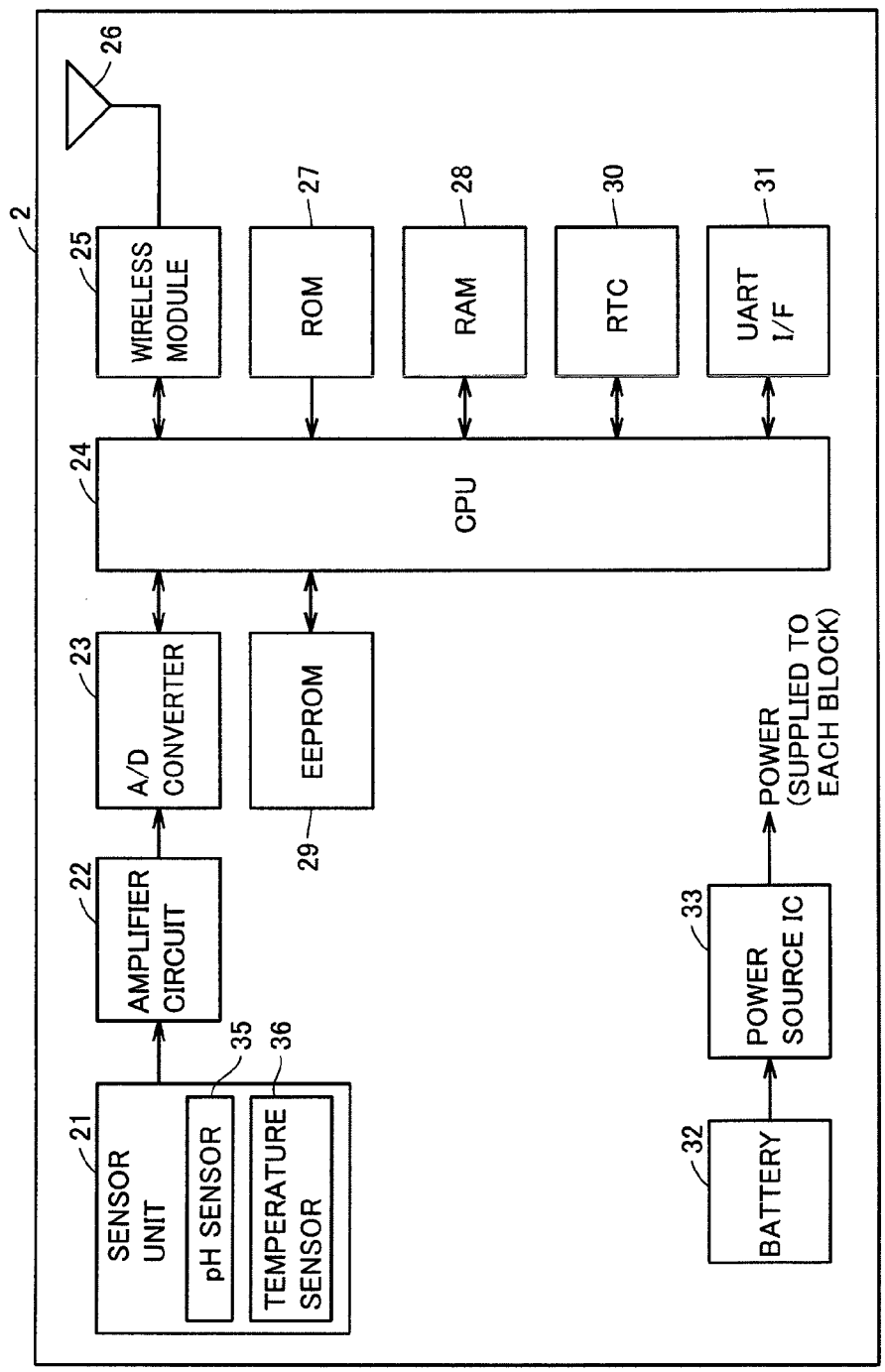
FIG. 2 is a circuit block diagram of a detection device 2 in accordance with the first embodiment of the present invention.

Next, components of monitoring system 100 shown in FIG. 1 will be described in detail. FIG. 2 is a circuit block diagram of detection device 2 in accordance with the first embodiment of the present invention.

Referring to FIG. 2, detection device 2 includes a sensor unit 21, an amplifier circuit 22, an A/D converter 23, a CPU (Central Processing Unit) 24, a wireless module 25, and an antenna 26.

Detection device 2 further includes an ROM (Read Only Memory) 27, an RAM (Random Access Memory) 28, an EEPROM (Electrically Erasable Programmable ROM) 29, an RTC (Real Time Clock) 30, an UART (Universal Asynchronous Receiver Transmitter) interface circuit 31, a battery 32, and a power source IC (Integrated Circuit) 33.

Sensor unit 21 includes a pH sensor 35 for measuring pH of the rumen liquid, and a temperature sensor 36 for measuring temperature of the rumen liquid for correcting the result of detection by pH sensor 35. The results of detection (results of measurements) by these sensors are output as analog signals.

Amplifier circuit 22 amplifies the analog signals output from sensor unit 21. A/D converter 23 converts the analog signals output from amplifier circuit 22 to digital signals.

CPU 24 is for generally controlling operations of detection device 2 and it outputs prescribed instructions to various units and components. By way of example, CPU 24 generates transmission data including the pH value, using the results of measurement by sensor unit 21 and the unique number of detection device 2 stored in EEPROM 29. ROM 27 is a storage area storing software program or programs used for realizing prescribed functions of CPU 24. RAM 28 is used as a work area of CPU 24.

Wireless module 25 is connected to antenna 26. Wireless module 25 and antenna 26 transmit the data sent from CPU 24 through wireless communication. On the other hand, wireless module 25 and antenna 26 receive information (radio signals) transmitted from outside through wireless communication.

EEPROM 29 is capable of storing information in a non-volatile manner and electrically rewriting stored information. As to the information stored in EEPROM 29, it is the information related to settings of detection device 2. By way of example, EEPROM 29 stores the unique number of detection device 2, data transmission schedule (for example, transmission interval or expected time of transmission) and so on. When new information is transmitted from setting unit 12, the information stored in EEPROM 29 is updated to the new information by CPU 24.

RTC is a circuit for time-keeping. CPU 24 obtains the current date and time (year, month, date and time) from RTC 30. UART interface circuit 31 converts asynchronous serial signals to parallel signals, or converts parallel signals to asynchronous serial signals. The asynchronous serial signals refer to radio signals transmitted or received by wireless module 25 and antenna 26. The parallel signals are the signals input to or output from CPU 24.

Each block shown in FIG. 2 may be provided separately or, by way of example, CPU 24, ROM 27, RAM 28, RTC 30, UART interface circuit 31 and the like may be integrated in one microcomputer.

Battery 32 and power source IC 33 supply electric power to each block of detection device 2. Battery 32 should preferably have as small volume as possible and as large battery capacity as possible. Smaller volume of battery 32 realizes reduction in size of detection device 2. Larger battery capacity of battery 32 makes longer the battery life and, therefore, the time period in which the state of rumen of the cow can be detected becomes longer, and the frequency of recovering detection device 2 from the rumen can be reduced. Therefore, in the first embodiment, a thionyl chloride lithium battery is used, for example, as battery 32. Further, from the viewpoint of battery life of battery 32, it is preferred that each block of detection device 2 has as small power consumption as possible.

Detection device 2 has a self-diagnostic function, and detects malfunction of sensor unit 21, voltage reduction of battery 32 or the like. If any abnormality is detected by the self-diagnostic function, detection device 2 transmits information related to the contents of abnormality through wireless communication.

Next, one specific example of the communication function of detection device 2 will be described. Frequency band of radio waves transmitted from detection device 2 and transmission output of detection device 2 are determined considering various factors including communication distance, battery life, influence on the biological body and so on. In the present embodiment, specifically, the radio waves transmitted from detection device 2 have frequency band of 429 MHz, and the transmission output is at most 10 mW.

Communication method of detection device 2 is half duplex, in which the direction of communication is switched. In other words, it is impossible for detection device 2 to simultaneously transmit and receive radio waves. Communication speed is, for example, 2400 bps, and the data format used for communication is binary data.

Figure 3:
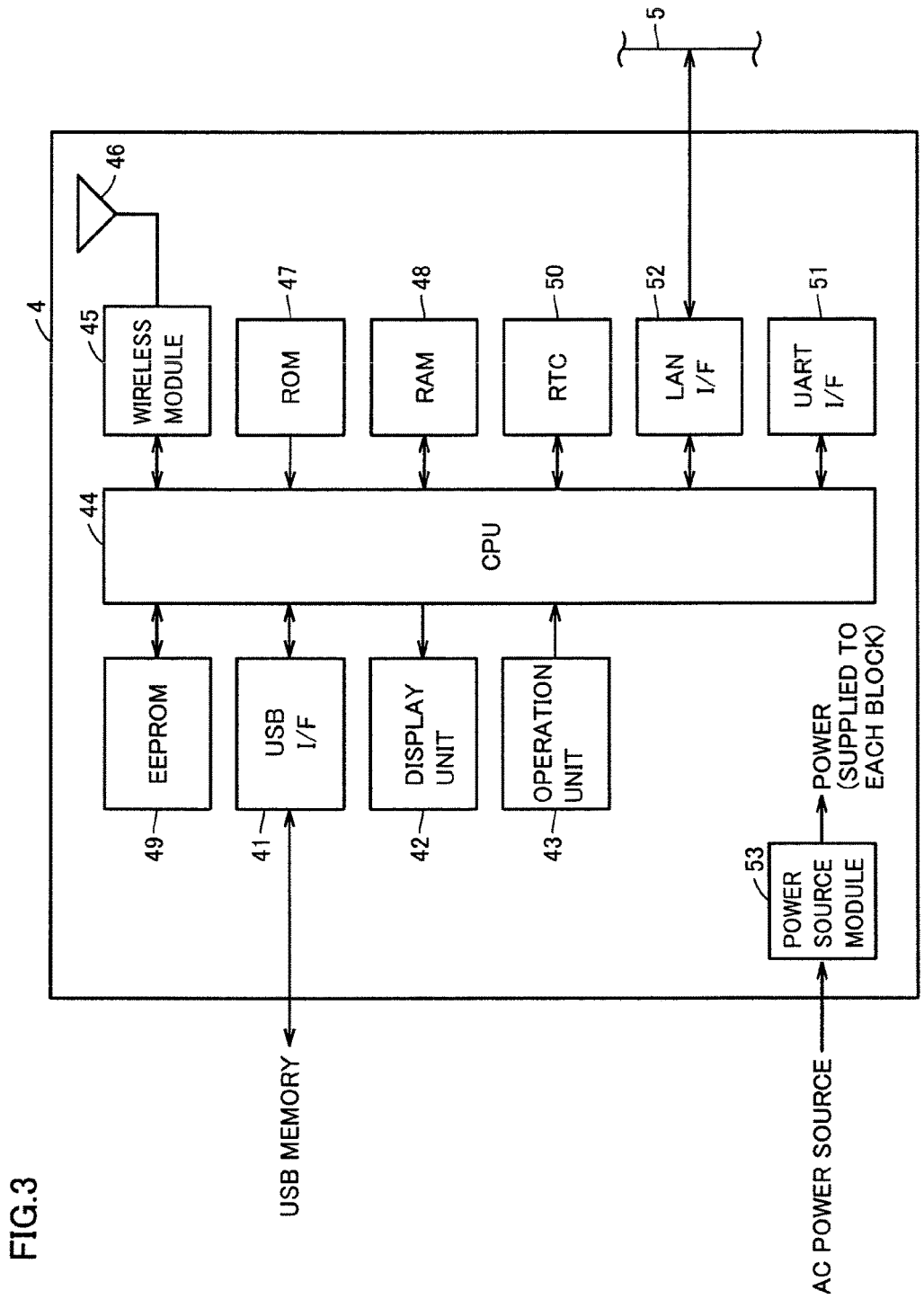
FIG. 3 is a circuit block diagram of a receiver 4 in accordance with the first embodiment of the present invention.

FIG. 3 is a circuit block diagram of a receiver 4 in accordance with the first embodiment of the present invention. Receiver 4 includes a USB interface circuit 41, a display unit 42, an operation unit 43, a CPU 44, a wireless module 45, and an antenna 46.

Receiver 4 further includes an ROM 47, an RAM 48, an EEPROM 49, an RTC 50, a UART interface circuit 51, a LAN interface circuit 52, and a power source module 53.

USB interface circuit 41 is a circuit for connecting an USB memory (external memory), not shown, to receiver 4. Display unit 42 is a circuit for displaying various pieces of information related to receiver 4, for example, state of operation of receiver 4, and it is implemented, for example, by a liquid crystal display circuit. Operation unit 43 is a circuit for receiving a user operation and includes, for example, a switch for turning the power on/off.

CPU 44 is for generally controlling operations of receiver 4. Functions of ROM 47 and RAM 48 are similar to the functions of ROM 27 or RAM 28 described above and, therefore, description thereof will not be repeated. Similar to RTC 30, RTC 50 is used by CPU 44 for obtaining the current date and time. UART interface circuit 51 converts asynchronous serial signals to parallel signals, or converts parallel signals to asynchronous serial signals. The asynchronous serial signals are radio signals received by wireless module 25 and antenna 26, and parallel signals are signals input to and output from CPU 44.

Wireless module 45 is connected to antenna 46. Wireless module 45 and antenna 46 receive information (radio signals) transmitted from detection device 2.

EEPROM 49 stores data received from detection device 2. EEPROM 49 is a non-volatile memory and, therefore, the data is not lost even in the case of power failure.

LAN interface circuit 52 is a circuit for exchanging data between receiver 4 and LAN 5.

Power source module 53 converts AC power from an AC power source to DC power, and supplies the DC power to each of the circuit blocks shown in FIG. 3.

The communication method of receiver 4 is half duplex. It is noted that receiver 4 only receives radio waves transmitted from detection device 2. Communication speed is, for example, 2400 bps, and the data format used for communication is binary data.

In receiver 4 (EEPROM 49), unique numbers of detection devices 2 as the objects of communication are registered in advance. Receiver 4 receives data including the unique number and the measurement values from detection device 2. If the unique number included in the received data matches any of the registered numbers, receiver 4 obtains the data and transmits the data to monitoring server 7 at prescribed timing. If the unique number included in the received data is different from the registered numbers, receiver 4 does not receive the data.

Figure 4:
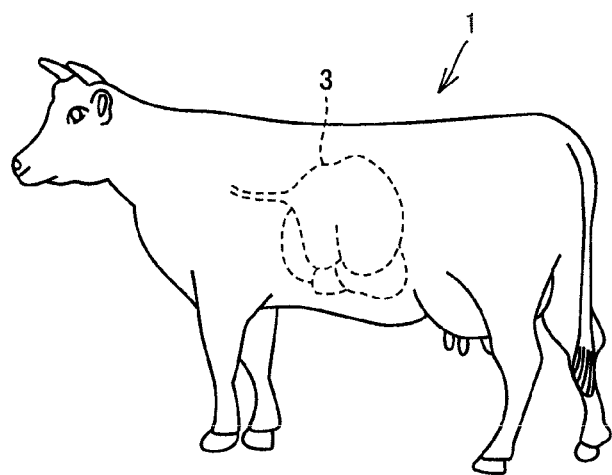
FIG. 4 is a side view of a cow 1 to which detection device 2 in accordance with the first embodiment of the present invention is administered.
Figure 5:
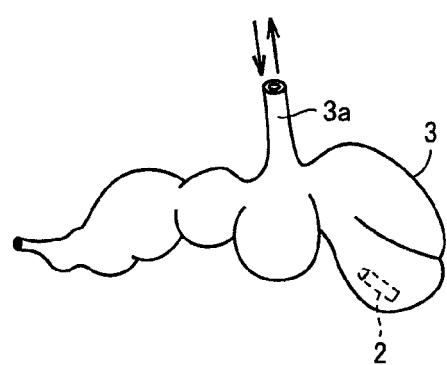
FIG. 5 schematically illustrates ruminant stomach of cow 1 of FIG. 4.

FIG. 4 is a side view of a cow 1 to which detection device 2 in accordance with the first embodiment of the present invention is administered. FIG. 5 schematically illustrates ruminant stomach of cow 1 of FIG. 4.

Referring to FIGS. 4 and 5, a cow has four stomach compartments. Among the four compartments, the largest is rumen 3. Detection device 2 administered orally to cow 1 passes through esophagus 3a and reaches rumen 3. Detection device 2 is adapted to have an appropriate weight to be retained in rumen 3. Further, detection device 2 is so configured as to allow recovery from rumen 3.

Figure 6:
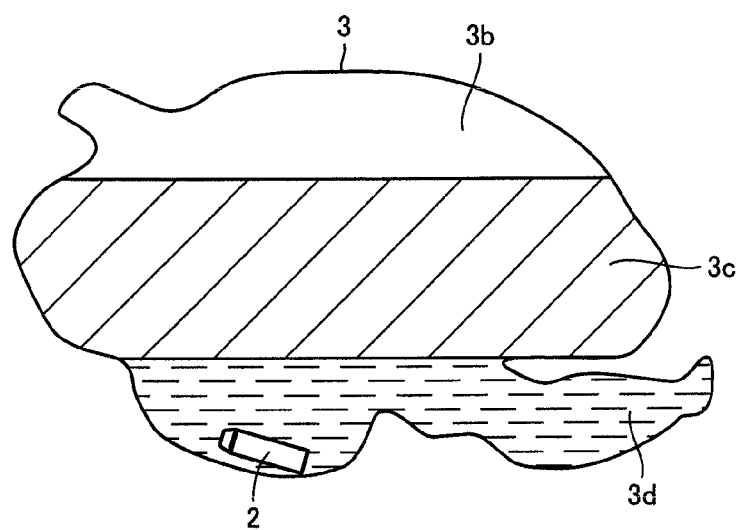
FIG. 6 is a schematic illustration showing the inside of cow's rumen.

FIG. 6 is a schematic illustration showing the inside of cow's rumen. Referring to FIG. 6, a large amount of feed stays in rumen 3, and the feed is decomposed by micro organisms living in rumen 3.

The inside of rumen 3 can roughly be classified to three layers, including an upper layer 3b, a middle layer 3c, and a lower layer 3d. Upper layer 3b is a gas layer filled with gases such as methane and carbon dioxide generated by fermentation. Middle layer 3c contains a large mass of feed referred to as a rumen mat. Lower layer 3d is a liquid layer in which small particles of feed are deposited. The orally administered detection device 2 reaches the inside of rumen 3, and is retained in lower layer 3d (liquid layer). In the present specification, the rumen liquid refers to the liquid component included in lower layer 3d, of the contents in the rumen.

Figure 7:
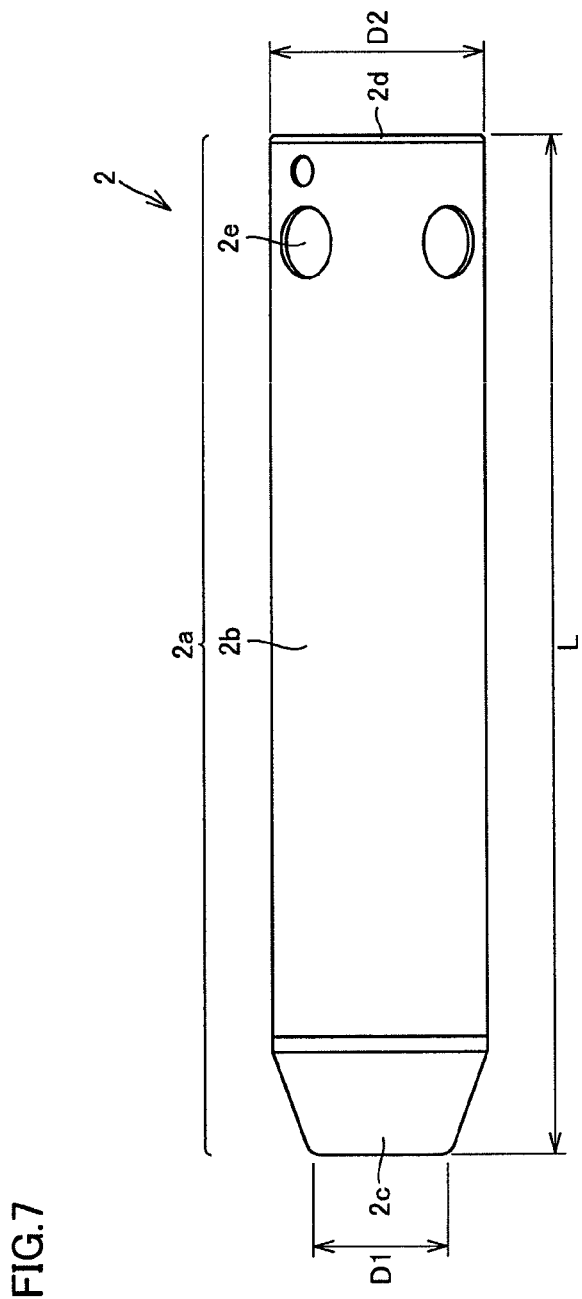
FIG. 7 is a perspective view showing an appearance of detection device 2 in accordance with the first embodiment of the present invention.

FIG. 7 is a perspective view showing an appearance of detection device 2 in accordance with the first embodiment of the present invention. Referring to FIG. 7, detection device 2 has a housing 2a containing each of the blocks shown in FIG. 2. Housing 2a has a cylindrical housing body 2b formed of metal, a cap 2c formed of resin, attached to one end of housing body 2b, and a coupling portion 2d attached to the other end of housing body 2b. An opening 2e for introducing the rumen liquid to the inside of housing 2a is formed in housing body 2b. Sensor unit 21 (not shown) contained in housing body 2b is brought into contact with the rumen liquid introduced from opening 2e to the inside of housing body 2b.

Housing 2a is formed of a material not eroded by the rumen liquid and having physical strength high enough to withstand movement and inner pressure of the rumen. Specifically, housing body 2b and coupling portion 2d are formed of stainless steel, and cap 2c is formed of resin (for example, polypropylene) having acid-resistance and strength high enough to withstand movement and inner pressure of the rumen.

Antenna 26 shown in FIG. 2 is housed in a space inside cap 2c. Since cap 2c is formed of resin, radio waves transmitted from or received by antenna 26 can pass through cap 2c.

Cap 2c has a tapered shape. Specifically, cap 2c is formed to be narrower toward its front edge. Diameter D1 of cap 2c at the front edge is made smaller than the diameter of tail edge of cap 2c connected to housing body 2b, that is, diameter D2 of housing body 2b. Therefore, housing 2a has a so-called bullet shape. By putting detection device 2a into the mouth of a cow with cap 2c facing forward, it becomes easier for the cow to swallow detection device 2.

Length L of housing 2a, diameter D1 at the front edge of cap 2c, and diameter D2 of housing body 2b are determined to be suitable for oral administration of detection device 2 to the cow. Specifically, for example, diameter D1 may be 20 mm, and diameter D2 may be 30 mm. If diameter D2 exceeds 30 mm, it becomes difficult to let the cow swallow detection device 2 and, therefore, diameter D2 is preferably 30 mm or smaller. The length L of detection device 2 is, for example, 130 to 150 mm.

The weight of detection device 2 is appropriately determined such that detection device 2 is retained in the rumen (specifically, in the liquid layer) of the cow. More specifically, in the first embodiment, the weight of detection device 2 is, for example, 120 to 150 g.

Coupling portion 2d is formed of a material that can be magnetically attachable, that is, a ferromagnetic or paramagnetic material. By way of example, coupling portion 2d is formed of ferromagnetic body, specifically, magnetic stainless steel (such as ferritic stainless steel). Coupling portion 2d may be formed by combining ferromagnetic and paramagnetic materials.

Figure 8:
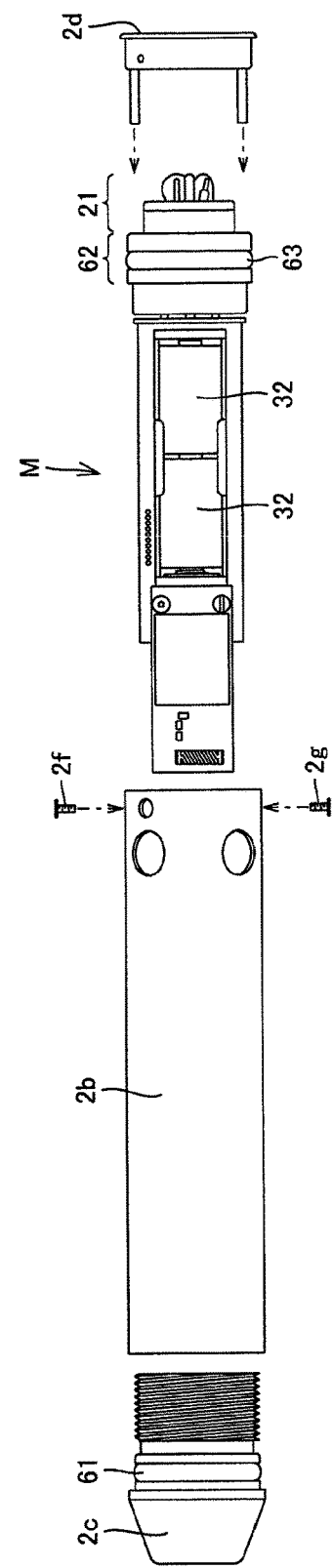
FIG. 8 is an exploded view of detection device 2 shown in FIG. 7.

FIG. 8 is an exploded view of detection device 2 shown in FIG. 7. Referring to FIG. 8, cap 2c and coupling portion 2d are formed to be detachable from housing body 2b. Screw is formed at one end on a side surface of cap 2c, to be fitted to thread (not shown) formed at an inner circumferential surface of housing body 2b. An O-ring 61 is provided on a side surface of cap 2c, in order to reliably prevent entrance of rumen liquid to housing body 2b.

Module M integrally implements the various circuit blocks shown in FIG. 2, and it can be taken out from the inside of housing body 2b. Module M has a separating portion 62 for separating the inside of housing body 2b to a first chamber containing sensor unit 21 and a second chamber containing portions other than sensor unit 21. Coupling portion 2d is fixed to housing body 2b by means of screws 2f and 2g.

The first chamber is a space defined by housing body 2b, coupling portion 2d and separating portion 62 (O-ring 63), and the second chamber is a space defined by housing body 2b, cap 2c and separating portion 62 (O-ring 63). Separating portion 62 includes O-ring 63. Since O-ring 63 is in contact with the inner circumferential surface of housing body 2b, entrance of rumen liquid to the second chamber can be prevented. Specifically, separating portion 62 is a protecting portion for preventing entrance of rumen liquid to the second chamber.

In the first embodiment, cap 2c, coupling portion 2d and separating portion 62 are all detachable from housing body 2b. In other words, the housing is formed to be opened and sealed at the portion where the second chamber is defined. With such a structure of the housing, it becomes possible to prevent portions other than sensor unit 21 in module M from contacting rumen liquid, and to take out module M from housing body 2b for exchanging battery 32 or for repairing module M.

What is necessary is that the portion defining the second chamber of the housing is formed to allow opening and sealing. Therefore, only the cap 2c may be made detachable from housing body 2b. With such a structure of the housing, module M may be formed, for example, such that the portion except for sensor unit 21 and separating portion 62 are removable from housing body 2b.

Figure 9:
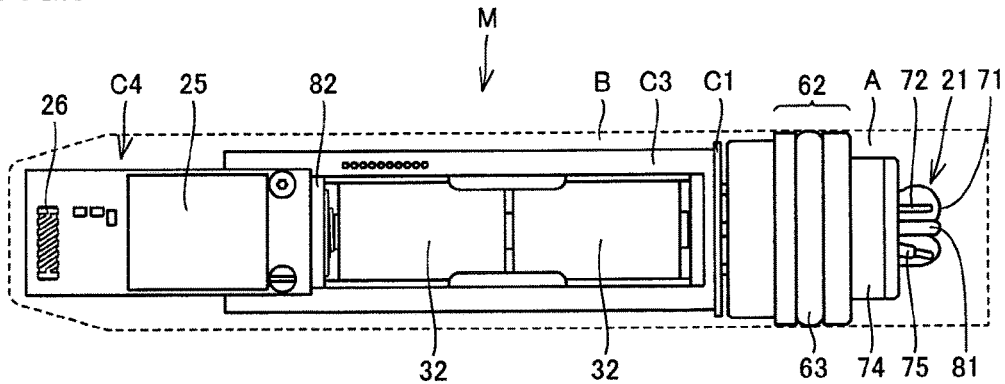
FIG. 9 is a first diagram schematically showing the configuration of a module M shown in FIG. 8.
Figure 10:
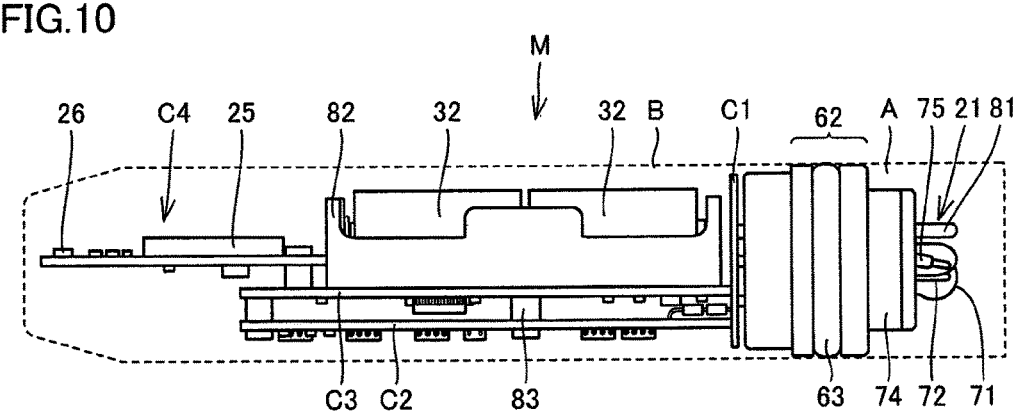
FIG. 10 is a second diagram schematically showing the configuration of module M shown in FIG. 8.

FIG. 9 is a first diagram schematically showing the configuration of module M shown in FIG. 8. FIG. 10 is a second diagram schematically showing the configuration of module M shown in FIG. 8.

Referring to FIGS. 9 and 10, the areas surrounded by dotted lines represent inner space of housing 2a. By separating portion 62 including O-ring 63, the inner space of housing 2a is divided into first chamber A and second chamber B.

Module M includes sensor unit 21 and circuit boards C1 to C4. Sensor unit 21 is placed in the first chamber A, while circuit boards C1 to C4 are placed in the second chamber B.

Sensor unit 21 includes a glass film 71, a glass electrode 72 arranged in a container formed by glass film 71, a comparison electrode (not shown) having at least a part arranged in an inner liquid (not shown), a porous resin 74 as a liquid junction, and a thermister 75 as a temperature sensor.

Each electrode of sensor unit 21 and the temperature sensor pass through the inside of separating portion 62 and are electrically connected to circuit board C1. Further, a ground electrode 81 is connected to circuit board C1.

Circuit board C2 is electrically connected to circuit board C1, and includes amplifier circuit 22 and A/D converter 23 shown, for example, in FIG. 2.

Circuit board C3 is electrically connected to circuit board C2 by means of a connector 83. Circuit board C3 includes CPU 24, ROM 27, RAM 28, EEPROM 29, RTC 30, UART interface circuit 31, battery 32, and power source IC 33, shown, for example, in FIG. 2. As described above, CPU 24, ROM 27 and RAM 28 may be integrated in one microcomputer. Two batteries 32 are held in a battery holder 82 and connected in series. Each battery has a voltage, for example, of 3.6V.

Circuit board C4 includes wireless module 25 and antenna 26, and is electrically connected to circuit board C3.

Figure 11:
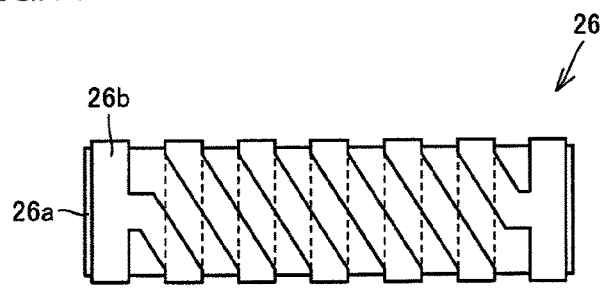
FIG. 11 shows an appearance of an antenna included in the detection device.

FIG. 11 shows an appearance of an antenna included in the detection device. Referring to FIG. 11, antenna 26 includes a dielectric chip 26a and a conductor 26b formed spirally on a main surface of dielectric chip 26a.

(Wireless Communication)

Where the monitoring system in accordance with the first embodiment of the present invention is operated in accordance with the Radio Law of Japan, wireless communication method using FM waves of 429 MHz band is used, and transmission power of detection device 2 is desirably set to 10 mW at the highest.

When radio wave of lower frequency band than the above is used, transmission time per data becomes longer as the communication speed slows, and there is a possibility of battery weakening. Further, because of longer wavelength, the antenna for transmission/reception must be made larger, or it becomes difficult to ensure a prescribed gain. When higher frequency band than the above is used, influence of electromagnetic wave on the biological body (cow) possibly increases. From these points of view, if the monitoring system in accordance with the first embodiment of the present invention is to be used in Japan, the frequency band of radio waves used for wireless communication should preferably be of 429 MHz band.

Further, in Japan, a radio station outputting radio waves having the frequency and power as mentioned above is classified to a specified low power radio station in accordance with the provision of the Radio Law. A specified low power radio station may operate any wireless equipment that received certificate of conformance to technical criteria, without any further qualification. Therefore, there would be less limitation related to the operation of the monitoring system.

When detection device 2 is not placed in the rumen, that is, when the wireless module is used outside the cow's body, the distance in which radio waves can stably be transmitted/received is relatively long. For instance, according to a preliminary experiment conducted by the inventors (communication experiment using a commercially available module), the communication distance was about 100 to about 150 m. The distance in which radio wave can be received from detection device 2 placed in the rumen, however, was 5 m at the longest.

The inventors studied the reason for such a phenomenon. In the rumen, detection device 2 is immersed in the rumen liquid and, therefore, it is considered that liquid surrounding detection device 2 serves as the ground. Further, cow's body, particularly the muscle and iron in the blood are considered to be functioning as a shield. The inventors concluded that the radio waves emitted from detection device attenuate from these reasons. Wireless communication was tried at a location of about 2 m away from the biological body, and it was found that the receiving intensity of the receiver attenuated significantly (for example, by about 10 dB) before and after the administration of detection device 2 to the rumen. When detection device 2 was placed in the rumen, it was difficult to distinguish noise from signals. In experiments using various antennas, it was difficult to attain comparable results as the wireless communication outside the cow's body.

The inventors considered two approaches as possible solutions to the problem above. One is a method of using a device having transmitter and receiver integrated together, and the other is a method of separately providing the transmitter and the receiver. In Japan, there is no standard designated by law on the gain of reception antenna, while a transmitter must be in compliance with the technical standard defined by the Radio Law.

According to the former approach, the radio waves can be received and transmitted by a single device and, therefore, the number of communication devices used for the monitoring system can be reduced. For collective management of a plurality of detection devices 2, however, it becomes necessary to elaborately select the place where the antenna is to be installed. Specifically, the distance between the antenna and the biological body (that is, communication distance), and the arrangement (for example, one antenna is to be placed at an equal distance from each of a number of cows) must be taken into consideration. Even if reception sensitivity is improved, it is difficult to reliably send setting information to the detection device placed in the rumen of a cow far away from the antenna, since transmission output is low.

According to the latter approach, since the transmitter and the receiver are formed separately, the communication function of the monitoring unit can be specialized to the receiving function. Therefore, it becomes possible to appropriately determine the arrangement and the number of receivers, taking into consideration the number of cows as the object of monitoring and the distance from the cows.

Since setting unit 12 is portable, it is possible to operate setting unit 12 near the cow body. Thus, possibility of radio waves not reaching detecting device 2 can be reduced. Further, once the operation conditions of detection device 2 are set, it is not likely that the operation conditions are to be changed afterwards. Therefore, though it is necessary for the user of setting unit 12 to come close to the biological body when operation conditions of detection device 2 placed in the rumen are to be changed, such a situation that requires change of settings is limited. Thus, operation of the monitoring system is facilitated.

In Japan, it is provided by the Radio Law that the antenna applied for the specified low power radio station must have the gain of at most 2.14 dBi. Therefore, in Japan, the antenna may be selected to satisfy the provision. On the other hand, there are no specific limiting conditions on a receiving antenna. Therefore, by specializing the communication function of the monitoring unit to the receiving function, degree of freedom in selecting the receiving antenna used for the monitoring unit can be increased. Further, the degree of freedom in selecting the place of installing the antenna can also be increased.

Since detection device 2 exists in the rumen, the radio wave that reaches antenna 46 of receiver 4 is weak. In order to improve reception sensitivity of receiver 4, the gain of antenna 46 of receiver 4 is made higher than the gain of antenna 26 of detection device 2. Further, considering the possibility that the radio waves reach antenna 46 from an arbitrary direction on a horizontal plane, antenna 46 should preferably be a horizontally non-directional antenna. A whip antenna, a ground plane antenna or a sleeve antenna may be used as antenna 46 as a horizontally non-directional antenna, and any antenna of the type that receives radio waves from antenna 26 with high gain may be used. By selecting antenna 46 of receiver 4 in accordance with the manner as described above, it becomes possible for receiver 4 to receive radio waves transmitted from detection device 2 with high reliability.

In the first embodiment, the communication device communicating wirelessly with detection device 2 is realized by separate receiver 4 and setting unit 12 (transmitter) as described above. It is noted, however, that if transmission output can be increased, that is, if the monitoring system in accordance with the present embodiment is used in an environment where regulations related to use of radio waves are less strict than the Radio Law mentioned above, a communication device having receiver 4 and setting unit 12 integrated with each other may be used.

(Sensor Unit)

Figure 12:
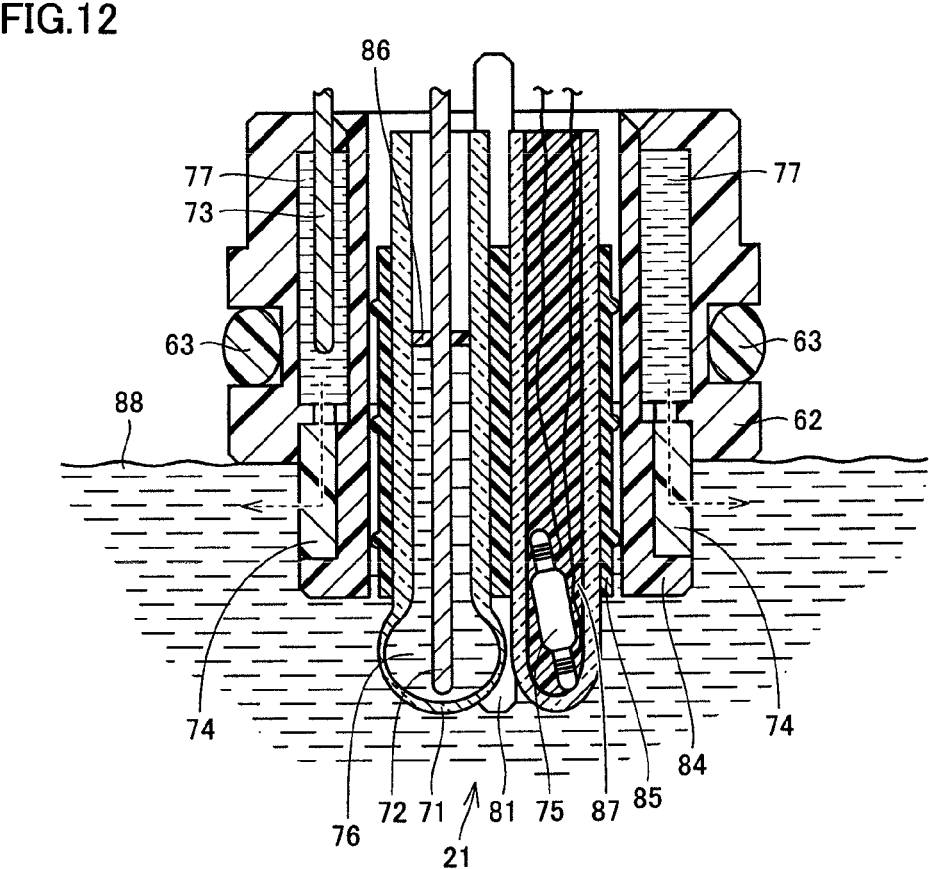
FIG. 12 is a cross-sectional view schematically illustrating the configuration of a sensor unit 21 in accordance with the first embodiment of the present invention.

FIG. 12 is a cross-sectional view schematically illustrating the configuration of sensor unit 21 in accordance with the first embodiment of the present invention. Referring to FIG. 12, sensor unit 21 includes a glass film 71, an internal buffer solution 76 filled in a container formed by glass film 71, a glass electrode 72 arranged in internal buffer solution 76, gel 77 filled in a space between separating portion 62 (outer case) and an inner case 84, a comparison electrode 73 arranged to be at least partially in contact with gel 77, porous resin 74 as a liquid junction, and thermister 75 as a temperature sensor. Sensor unit 21 is inserted to a holder 85, and holder 85 is fixed inside inner case 84. Glass film 71, internal buffer solution 76, glass electrode 72, gel 77, comparison electrode 73 and porous resin 74 constitute pH sensor 35 shown in FIG. 2.

Internal buffer solution 76 is specifically a potassium chloride (KCl) solution (for example, 3.3 mol/L-KCl solution, KCl saturated solution or the like). Internal buffer solution 76 is sealed in the container formed by glass film 71 by means of a packing 86. Thermister 75 is fixed and sealed by silicone filler 87.

Glass film 71 and porous resin 74 are brought into contact with rumen liquid 88. As represented by dotted arrows, the inner liquid of gel 77 gradually flows out little by little through the space between separating portion 62 (outer case) and inner case 84 and through porous resin 74 as the liquid junction.

Since the outer wall of glass film 71 is in contact with the liquid to be measured, that is, the rumen liquid 88, electromotive force generates between the inner and outer walls of glass film 71. Potential difference between comparison electrode 73 and glass electrode 72 is equal to the electromotive force in proportion to the pH of liquid to be measured plus the difference between the single electrode potential of glass electrode 72 and the single electrode potential of comparison electrode 73. Since glass electrode 72 and comparison electrode 73 are both in contact with KCl solution, the difference between single electrode potential of glass electrode 72 and single electrode potential of comparison electrode 73 becomes 0. Therefore, by detecting the potential difference between glass electrode 72 and comparison electrode 73, electromotive force in proportion to the pH of rumen liquid can be detected. The electromotive force changes depending on temperature and, therefore, temperature change in the electromotive force is corrected based on the result of detection by thermister 75.

Well-known pH sensors include a glass electrode type pH sensor used in the first embodiment of the present invention, and an Is-FET sensor (ion-sensitive Field Effect Transistor) sensor. The inventors first tried the Is-FET sensor as a sensor to be mounted on detection device 2. The sensor, however, is intended for batch measurements (intermittent measurements) and, therefore, it is difficult to maintain its performance while keeping it in contact with liquid sample for a long time. From the result of preliminary experiment by the inventors, the life of an Is-FET sensor was estimated to be at most 500 hours.

In contrast, a glass electrode type pH sensor can measure the pH of a liquid while the glass thin film is constantly kept in contact with the liquid. From these reasons, in the present embodiment, a glass electrode type pH sensor is adopted. Sensor unit 21 is housed in a housing body 2b as a metal cylinder, and the rumen liquid introduced to the inside of housing body 2b through opening 2e contacts glass film 71. The size of opening 2e is determined to be such a size that can prevent passage of undigested feed or a cow magnet (powerful magnet for attracting tramp iron) through opening 2e. Thus, of the contents of rumen, only the rumen liquid is introduced to the inside of housing body 2b, and hence, damage to glass film 71 can be prevented.

Further, in the first embodiment of the present invention, the liquid junction is formed of porous resin, more specifically of porous Teflon (registered trademark). For industrial pH sensors (glass electrode type pH sensors), generally, porous ceramics are used for the liquid junction of the comparison electrode. The pores of ceramics, however, are very fine, so that the liquid junction may possibly be clogged by food particles contained in the rumen liquid. In contrast, pores of porous Teflon (registered trademark) are generally larger than the pores of porous ceramics. Further, Teflon (registered trademark) has low affinity to other substance such as water and, therefore, amount of dirt deposited on the liquid junction can be reduced. Thus, clog of liquid junction can be prevented and, hence, measurement of pH of rumen liquid for a long period of time is possible.

Further, in the first embodiment of the present invention, gelated internal solution is used. Typically, the internal solution is liquid. The inventors conducted experiment of continuously measuring pH in the rumen. In about two days from the start of experiment, pH measurements became unstable, and finally, measurement failed. The sensor that failed was recovered and the cause of failure was studied. It was found that the internal solution was completely lost.

The inventors thought that the amount of liquid junction (amount of flow out) increased since the temperature in the rumen was around 40° C. and relatively high, and as a result, the internal solution was exhausted in a short period. Therefore, the inventors tried internal solution gelated by a gelator. The gelator used here was hydroxyethyl cellulose, and the duration of pH measurement could be extended to about ten days. In about two weeks, however, measurements became unstable. The inventors examined the phenomenon, and it was found that the gelator was decomposed by cellulose degrading bacteria in the rumen liquid.

The cellulose degrading bacteria in the rumen decomposes cellulose and generates, for example, acetic acid. It was considered that the gel was consumed in a short period because of the action of the bacteria. From the results of these experiments, in the present embodiment, the internal solution (KCl solution) is gelated using a gelator not susceptible to the decomposing function of cellulose degrading bacteria. As a result, the amount of flow out of internal solution in the rumen can be reduced and, therefore, measurement of rumen pH for a long period becomes possible.

As the gelator mentioned above, in the present embodiment, xanthane gum is used. Xanthane gum is a food additive, popularly used in foods. Thus, influence to biological body is small.

(Method of Recovering the Detection Device)

Figure 13:
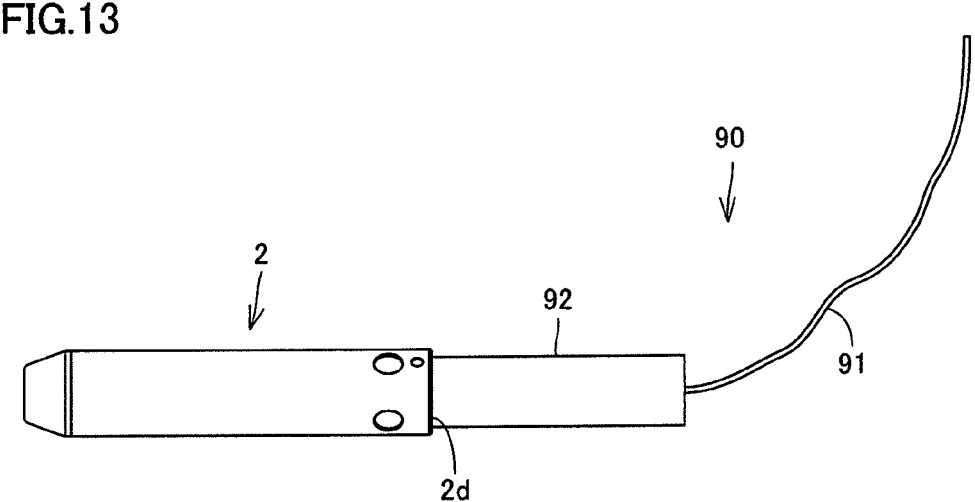
FIG. 13 schematically illustrates a recovery instrument for recovering detection device 2 in accordance with an embodiment of the present invention.

FIG. 13 schematically illustrates a recovery instrument for recovering detection device 2 in accordance with an embodiment of the present invention. Referring to FIG. 13, recovery instrument 90 includes a metal wire 91 and a magnet 92 attached to the tip end of wire 91. A metal chain or a metal tube may be used in place of wire 91. Wire 91 is sufficiently longer than the length from the mouth to the rumen of the cow. Since coupling portion 2d of detection device 2 is formed of paramagnetic or ferromagnetic body, coupling portion 2d is attracted to magnet 92. Thus, detection device 2 can be taken out from the rumen. As recovery instrument 90 having such a structure, for example, a magnet with a chain, may be used.

Detection device 2 (coupling portion 2d) may be configured to be coupled to the recovery instrument used. If it is possible that a manipulator is used as recovery instrument 90, coupling portion 2d may be formed to be engageable to the manipulator.

Figure 14:
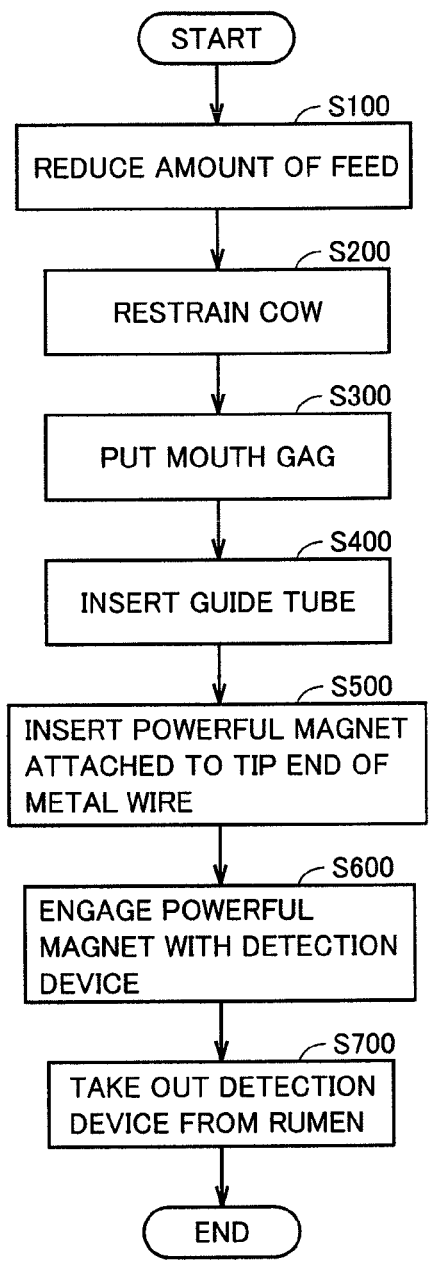
FIG. 14 is a flowchart representing a method of recovering the detection device in accordance with an embodiment of the present invention orally from the rumen of a cow.

FIG. 14 is a flowchart representing a method of recovering detection device 2 in accordance with an embodiment of the present invention orally from the rumen of a cow.

Referring to FIG. 14, at step S100, the amount of feed fed to the cow is reduced. Specifically, from the evening the previous day of recovery of detection device from the cow, feeding is completely stopped, or the amount of feed is limited to about half the normal amount.

On the day of recovery of detection device 2 from the cow, the process of steps S200 to S700 is executed. At step S200, the cow is restrained, and the cow is watered with a sufficient amount, for example, 20 to 40 liters, of water.

At step S300, a mouth gag is put on cow's mouth. At step S400, a guide tube formed, for example, of vinyl chloride is inserted through the mouth to the throat of the cow.

At step S500, a powerful magnet attached to the tip end of metal wire is inserted to the rumen through the guide tube. The powerful magnet that entered the rumen reaches the solid body layer in the rumen (corresponding to middle layer 3c shown in FIG. 6) and then sinks to the liquid layer at the lower part of the rumen (corresponding to lower layer 3d shown in FIG. 6) because of its own weight.

At step S600, detection device 2 is coupled to the powerful magnet. As shown in FIG. 6, detection device retained in rumen 3 normally exists in the liquid layer (ventral sac) at the lower portion of the rumen. When the powerful magnet reaches the liquid layer, coupling portion 2d of detection device 2 attaches to the magnet. Thus, detection device 2 is engaged with the powerful magnet.

At step S700, detection device 2 coupled to the powerful magnet is gently pulled and detection device 2 is passed through the solid body layer in the rumen, cardiac opening and the mouth. Thus, detection device 2 is recovered.

As the amount of feed to the cow is reduced or the cow is fasted before recovering detection device 2 as indicated at step S100, the contents in the rumen (particularly, the solid body) can be reduced. This facilitates searching, pulling and recovery of detection device 2. Thus, if the function of detection device stops because of circuit failure or battery exhaustion, for example, the detection device can be recovered.

As described above, according to the first embodiment, the inner state of cow's rumen can be detected accurately on real time basis. Further, the inner state of cow's rumen can easily be monitored. Further, since the detection device can be re-used, system cost can be reduced.

Since pH of cow's rumen can be measured accurately, it becomes possible for the farmer to improve nutrition management while grasping the state of feeding management. Further, since the rumen pH can be measured and monitored continuously for a long period, it is possible to prevent rumen acidosis and related diseases such as various metabolic diseases, infectious diseases or hoof diseases.

Embodiment 2

Figure 15:
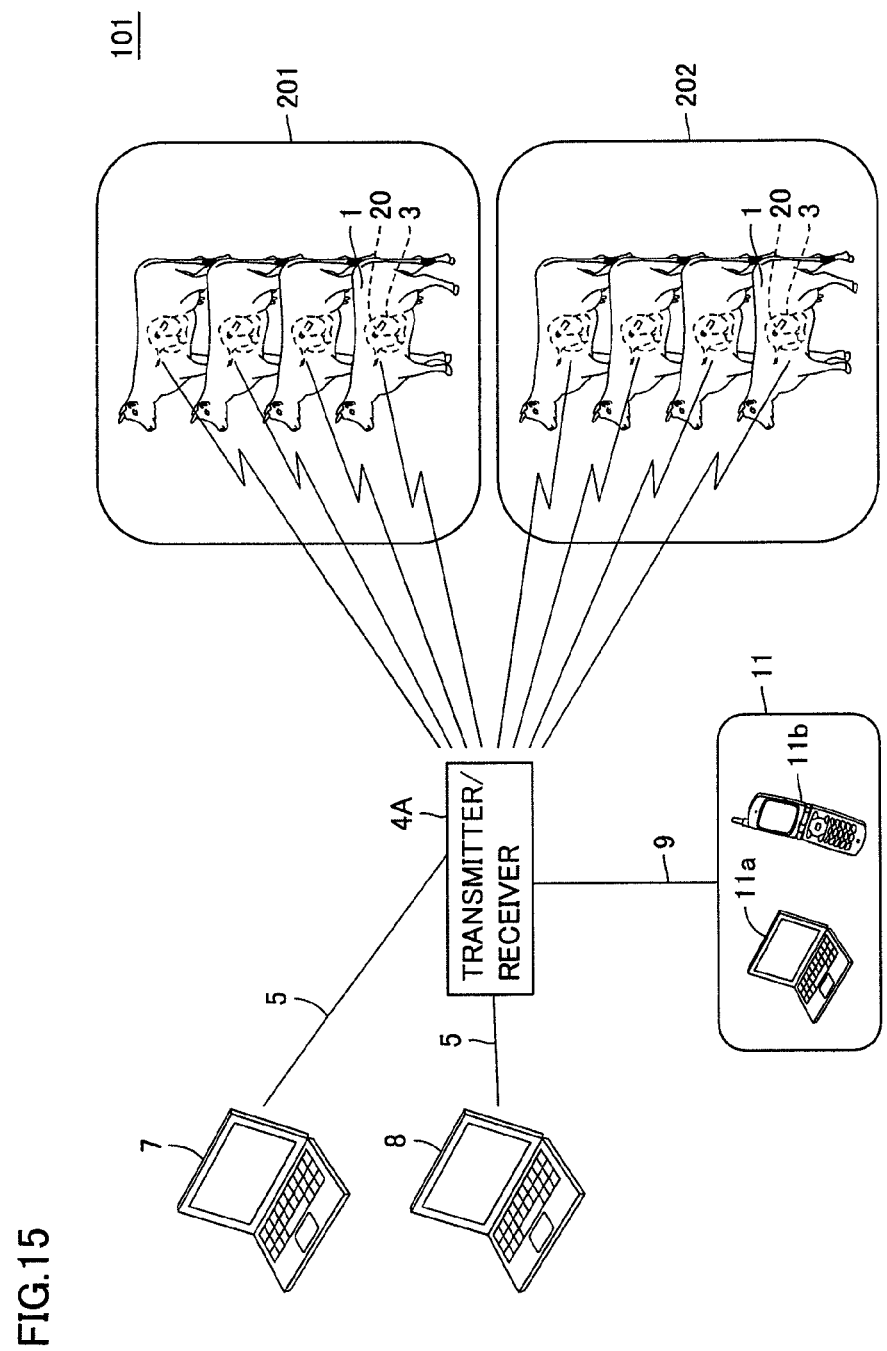
FIG. 15 schematically shows an overall configuration of a monitoring system 101 in accordance with a second embodiment of the present invention.

FIG. 15 schematically shows an overall configuration of a monitoring system 101 in accordance with a second embodiment of the present invention. Referring to FIG. 15, a monitoring system 101 in accordance with the second embodiment of the present invention is different from monitoring system 100 in accordance with the first embodiment in that it includes a transmitter/receiver 4A in place of receiver 4 and setting unit 12. Further, monitoring system 101 is different from monitoring system 100 in that it includes a detection device 20 in place of detection device 2.

Transmitter/receiver 4A is installed, for example, in a livestock barn. Transmitter/receiver 4A has functions of both the setting unit 12 and receiver 4. Specifically, transmitter/receiver 4A transmits an instruction for calibrating detection device 20 (sensor), a command for setting transmission frequency and the like through wireless communication to detection device 20. Further, transmitter/receiver 4A receives data related to pH in the rumen measured by detection device 20 through wireless communication from detection device 20. Further, if reception of data transmitted from detection device 20 is successful, transmitter/receiver 4A transmits an acknowledgement data to detection device 20.

Figure 23:
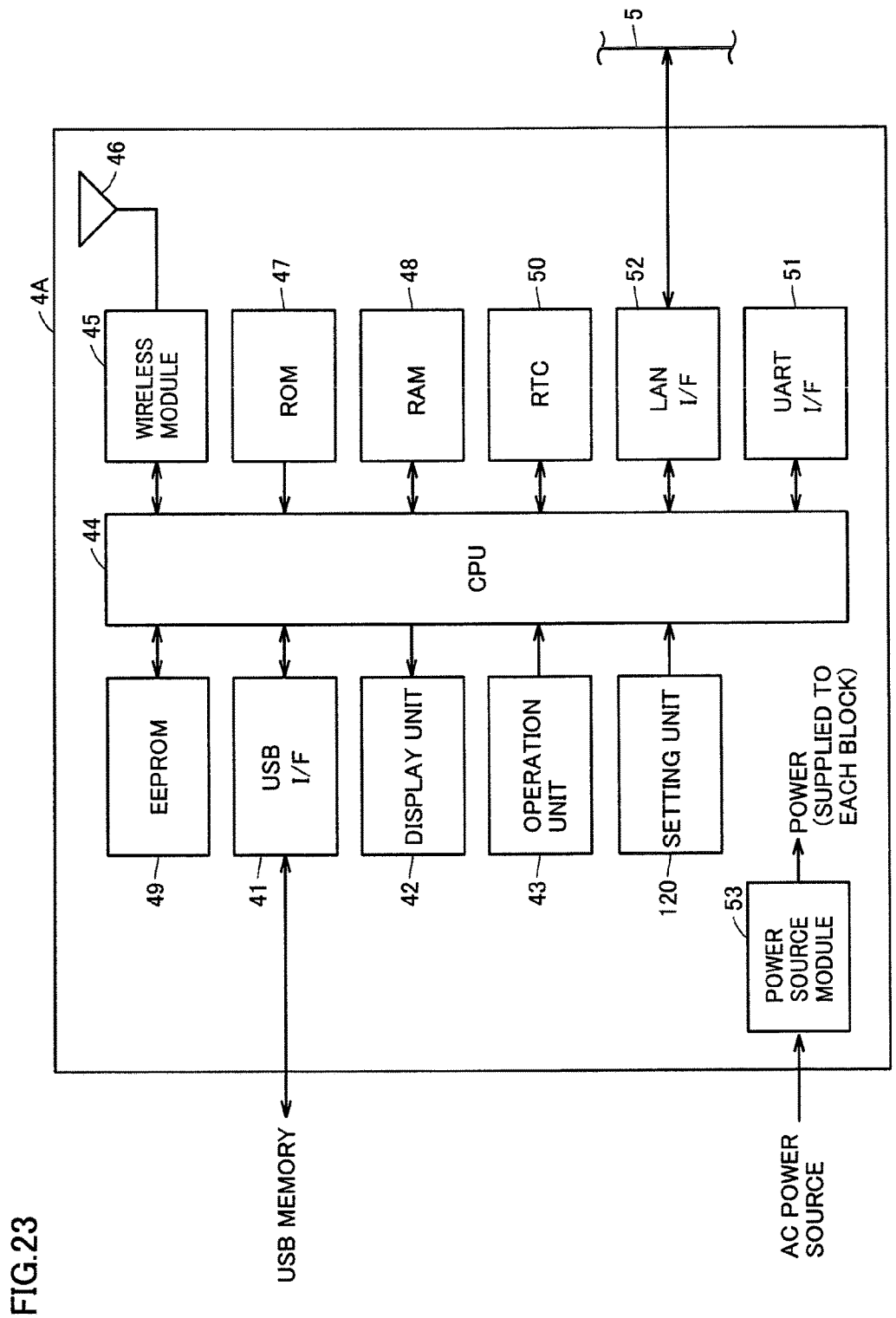
FIG. 23 is a functional block diagram of a transmitter/receiver 4A.

FIG. 23 is a functional block diagram of a transmitter/receiver 4A. Referring to FIGS. 23 and 3, the configuration of transmitter/receiver 4A is different from that of receiver 4 in that it additionally includes a setting unit 120. Setting unit 120 has the same function as setting unit 12. As in the first embodiment, it is preferred that the gain of antenna 46 is higher than that of the antenna of detection device 20.

When the acknowledgement data is received, detection device 20 ends transmission of measurement data. If the acknowledgement data is not received after the transmission of measurement data from detection device 20, detection device 20 repeats transmission of the same data. The maximum number of repetition is determined in advance by a command from transmitter/receiver 4A, and it is, for example, three times. When the number of transmissions reached the maximum number of times and still the acknowledgement data cannot be received, detection device 20 stops data transmission. Since the number of repetitive transmission of data by detection device 20 is limited, power consumption by detection device 20 can be reduced. This elongates the duration of battery power, and hence, elongates the operation period of detection device 20.

Detection device 20 transmits the measurement data (pH value) through wireless communication at a constant time interval (for example, at every 10 minutes). In accordance with a command or commands sent from transmitter/receiver 4A, detection device 20 executes various processes such as sensor calibration, setting of data measurement frequency (time interval) and setting of the number of repetitive transmissions if data reception by transmitter/receiver 4A failed.

A relay (repeater) for relaying wireless communication between transmitter/receiver 4A and detection device 20 may be added to monitoring system 101. This reduces the possibility of unsuccessful wireless communication between transmitter/receiver 4A and detection device 20.

As in the first embodiment, detection device 20 is configured to be recoverable from rumen 3. Detection device 20 is recovered orally from rumen 3 of cow 1 in accordance with the flowchart shown in FIG. 14.

Figure 16:
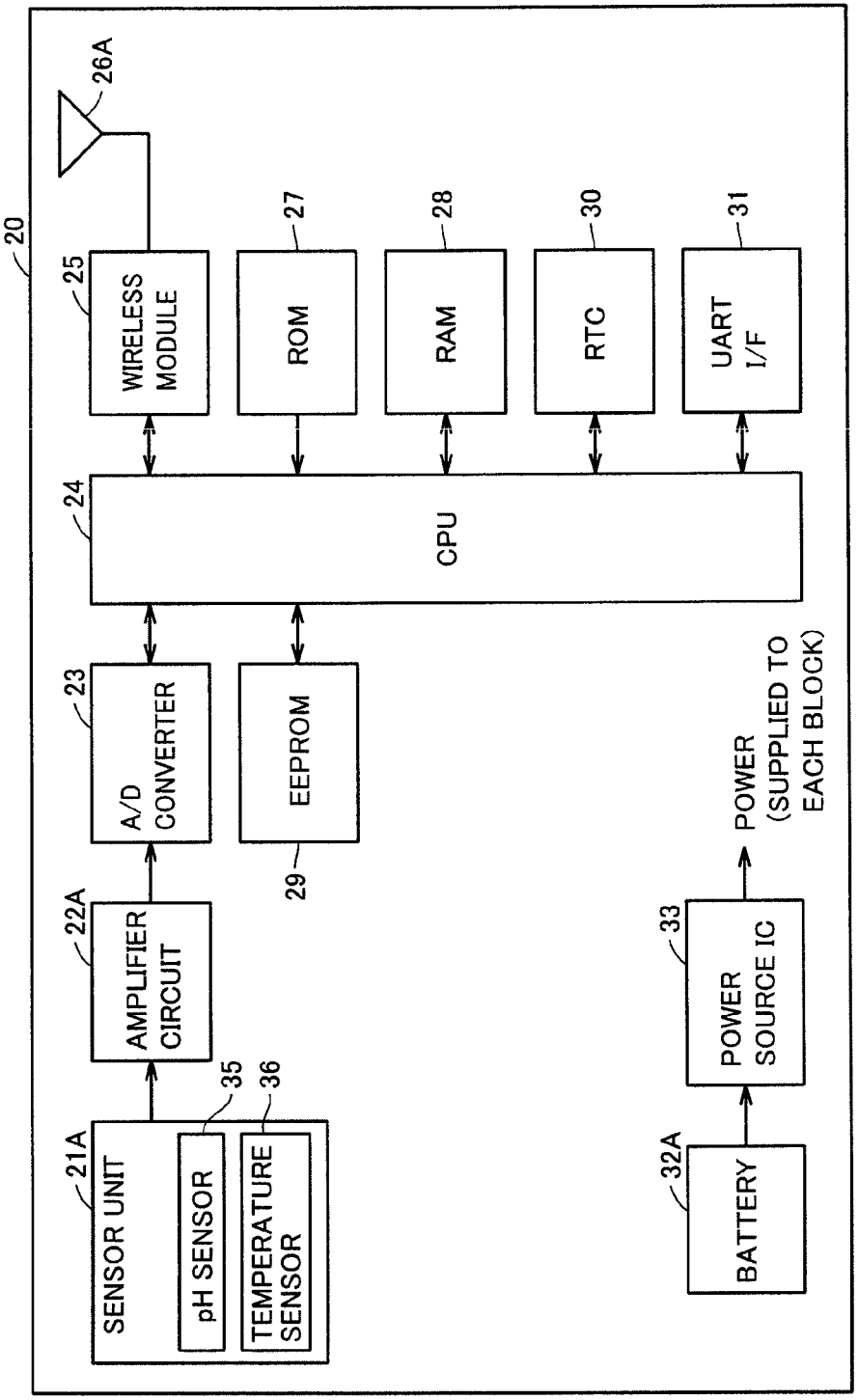
FIG. 16 is a functional block diagram of a detection device 20 shown in FIG. 15.

FIG. 16 is a functional block diagram of a detection device 20 shown in FIG. 15. Referring to FIGS. 16 and 2, the configuration of detection device 20 is basically the same as that of detection device 2 in accordance with the first embodiment. It is noted, however, that detection device 20 has a sensor unit 21A, an amplifier circuit 22A, an antenna 26A and a battery 32A, in place of sensor unit 21, amplifier circuit 22, antenna 26 and battery 32. In this point, detection device 20 is different from detection device 2.

The appearance of detection device 20 is similar to the appearance (see FIG. 7) of detection device 2 and, therefore, detailed description related to the appearance of detection device 20 will not be repeated hereinafter. In the following, the differences between detection device 20 and detection device 2 will be described in detail.

Figure 17:
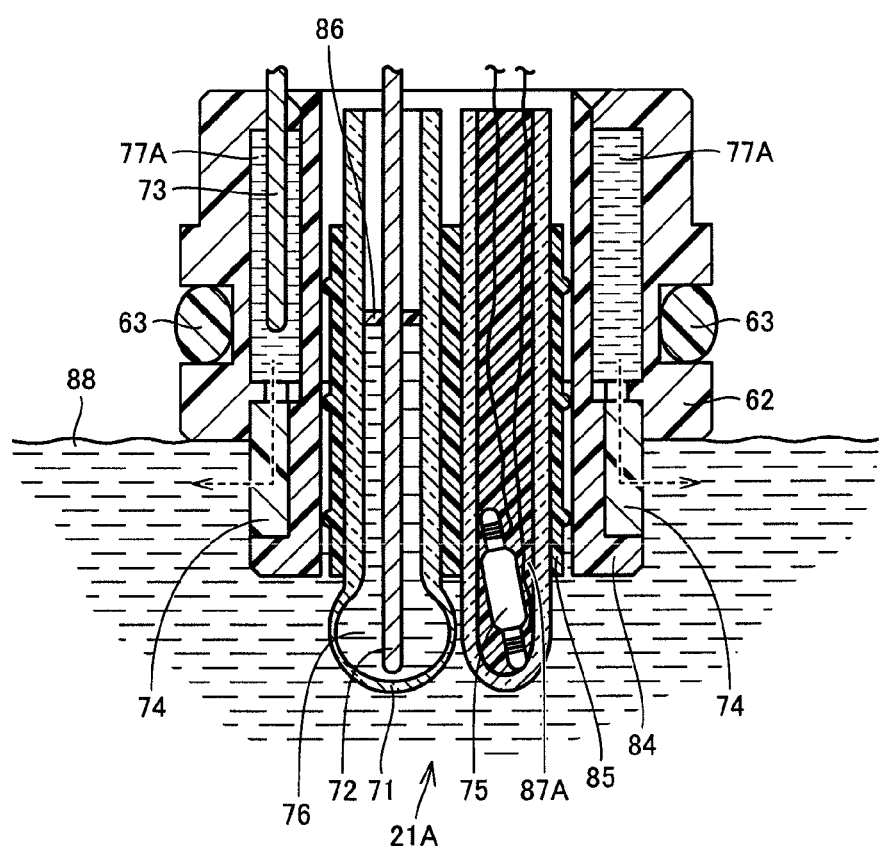
FIG. 17 is a cross-sectional view schematically showing the configuration of sensor unit 21A.

FIG. 17 is a cross-sectional view schematically showing the configuration of sensor unit 21A. Referring to FIG. 17, sensor unit 21A includes internal solution 77A. In the second embodiment, internal solution 77A is not gelated but in the liquid form. Specifically, internal solution 77A is potassium chloride saturated solution. Since the saturated solution is used as the internal solution, it follows that the internal solution only flows out through the liquid junction (porous resin 74). This can prevent change in concentration (KCl concentration) of internal solution and, therefore, measurement values of detection device 20 can be made stable. Since the measurement values of detection device 20 are made stable, the period of measurement can be made longer.

Further, in the second embodiment, in order to seal and fix thermister 75, magnesia 87A is used in place of silicone filler 87. Since thermister 75 is sealed and fixed by means of magnesia 87A, temperature sensitivity of thermister 75 can be improved than in the first embodiment.

Further, in the second embodiment, sensor unit 21A does not have ground electrode 81. As will be described in detail later, in the second embodiment, non-differential amplification method is used as the method of amplification by amplifier circuit 22A. Thus, ground electrode 81 can be omitted from sensor unit 21A.

Configuration of other portions of sensor unit 21A is the same as that of sensor unit 21 in accordance with the first embodiment and, therefore, description thereof will not be repeated.

Figure 18:
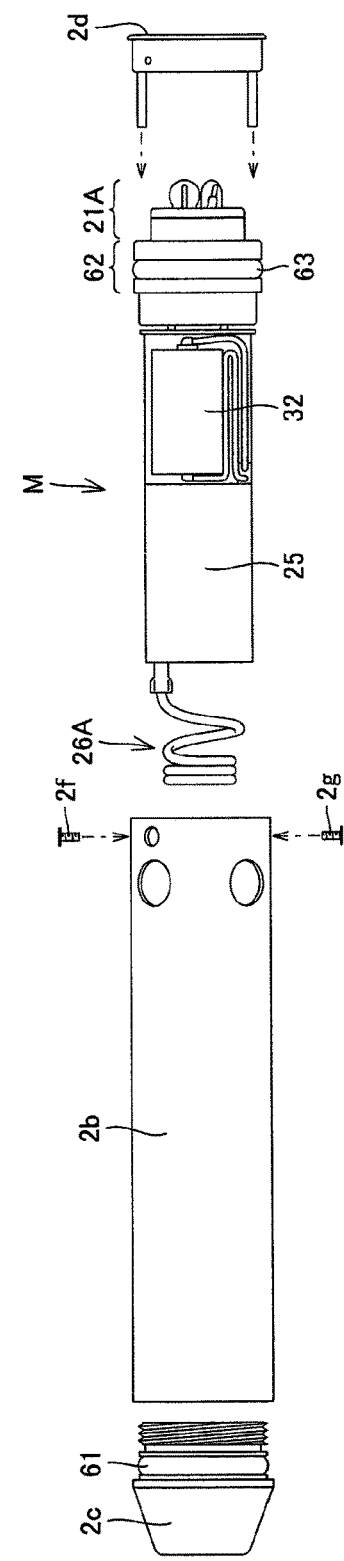
FIG. 18 is an exploded view of detection device 20 in accordance with the second embodiment of the present invention.
Figure 19:
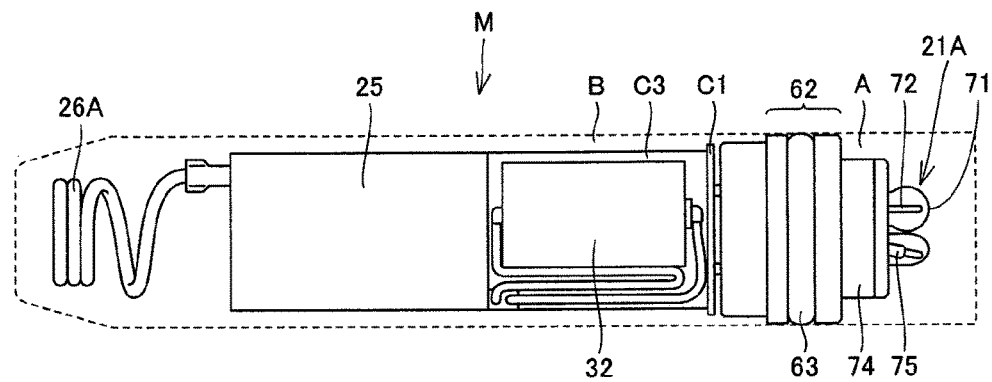
FIG. 19 is a first illustration schematically showing the configuration of module M shown in FIG. 18.
Figure 20:
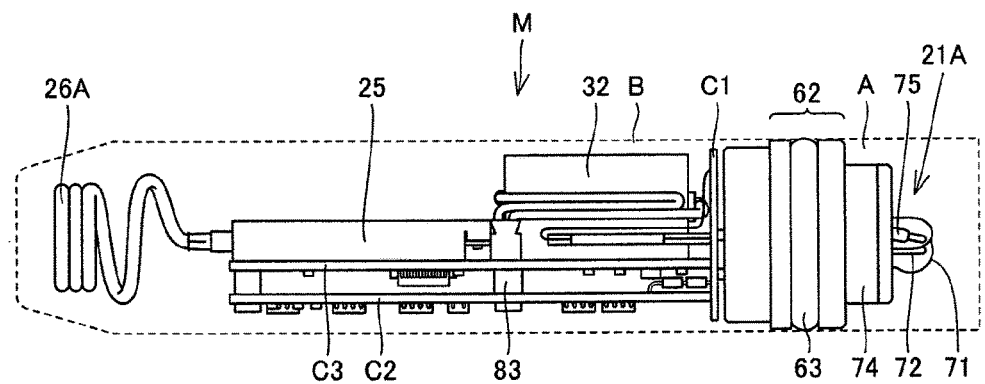
FIG. 20 is a second illustration schematically showing the configuration of module M shown in FIG. 18.

FIG. 18 is an exploded view of detection device 20 in accordance with the second embodiment of the present invention. FIG. 19 is a first illustration schematically showing the configuration of module M shown in FIG. 18. FIG. 20 is a second illustration schematically showing the configuration of module M shown in FIG. 18.

Referring to FIGS. 18 to 20, module M includes sensor unit 21A and circuit boards C1 to C3. Wireless module 25 is mounted on circuit board C3. Antenna 26A is a λ/4 whip antenna including a spirally wound conductor.

Detection device 2 in accordance with the first embodiment has circuit board C4 mounting wireless module 25 and antenna 26. In contrast, in the second embodiment, wireless module 25 is mounted on circuit board C3 and antenna 26A is implemented by a whip antenna. Thus, circuit board C4 can be omitted from detection device 20.

Further, in detection device 2 in accordance with the second embodiment, one battery 32A is used. As in detection device 2 in accordance with the first embodiment, battery 32A is, for example, a thionyl chloride lithium battery. The voltage of battery 32A is, for example, 6V. Capacity of battery 32 is, for example, 1700 mAh.

Configuration of other portions of module M shown in FIGS. 18 to 20 is the same as the configuration of corresponding portions of module M in accordance with the first embodiment and, therefore, description thereof will not be repeated.

The weight of detection device 20 is appropriately determined such that detection device 20 is retained in the rumen (specifically, in the liquid layer) of the cow. More specifically, in the second embodiment, the weight of detection device 20 is, for example, 160 to 200 g.

As described above, in the second embodiment, as the method of amplification of amplifier circuit 22A, non-differential amplification method is used. This reduces power consumption of amplifier circuit 22A. Further, it becomes possible to remove ground electrode from sensor unit 21A.

Figure 21:
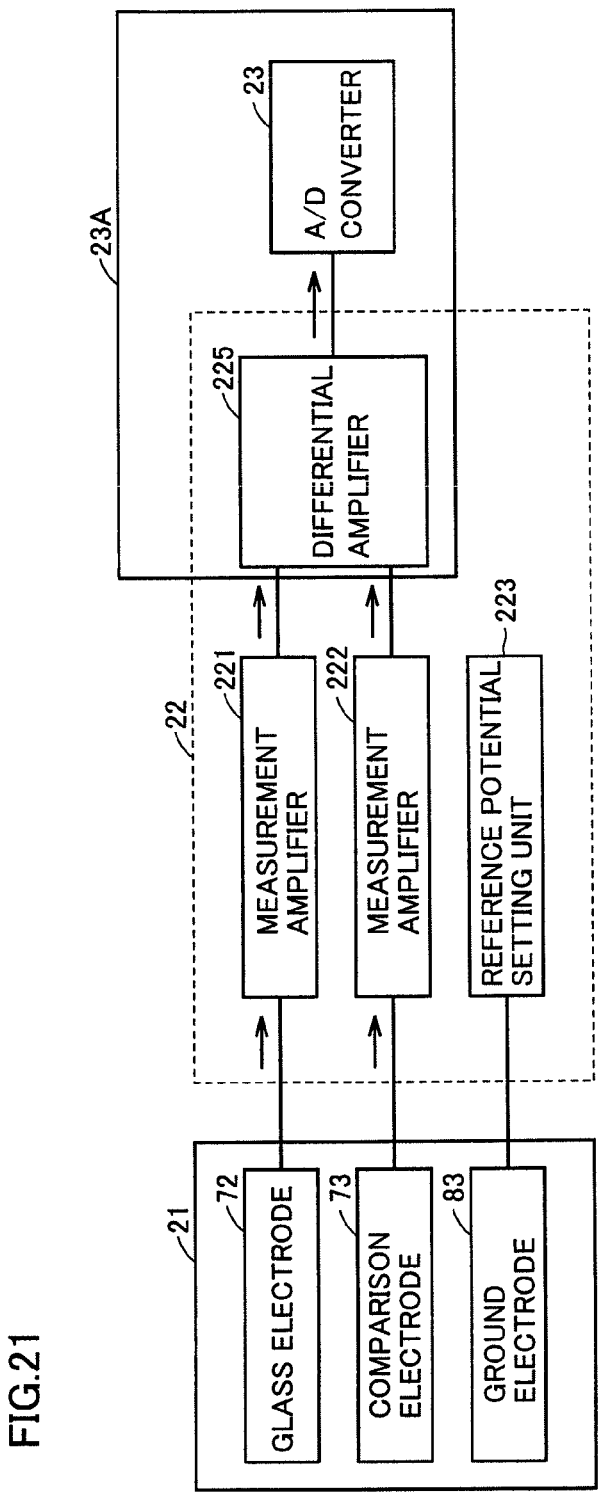
FIG. 21 is a functional block diagram of an amplifier circuit 22 in accordance with the first embodiment.

FIG. 21 is a functional block diagram of an amplifier circuit 22 in accordance with the first embodiment. Referring to FIG. 21, amplifier circuit 22 includes measurement amplifiers 221 and 222, a reference potential setting unit 223, and a differential amplifier 225. It is noted that in module M shown in FIGS. 8 to 10, differential amplifier 225 and A/D converter 23 constitute A/D converting circuit 23A and integrated as a module.

Sensor unit 21 has glass electrode 72, comparison electrode 73 and ground electrode 81.

Measurement amplifier 221 is an amplifier for measuring potential of glass electrode 72. Measurement amplifier 222 is an amplifier for measuring potential of comparison electrode 73. Differential amplifier 225 amplifies potential difference between output potential of measurement amplifier 221 and output potential of measurement amplifier 222. The output of differential amplifier 225 is transmitted to A/D converter 23.

In the first embodiment, ground electrode 81 is connected to reference potential setting unit 223. In this case, the reference of each of the potentials of glass electrode 72 and comparison electrode 73 is the potential of ground electrode 81. Differential amplifier 225 amplifies the potential difference between output potentials of measurement amplifiers 221 and 222.

In the first embodiment, differential amplifier 225 is operated in accordance with differential amplification method. Specifically, differential amplifier amplifies the potential difference between outputs of measurement amplifiers 221 and 222. This method requires two measurement amplifiers and, therefore, power consumption of the amplifier circuit as a whole becomes large. This may lead to earlier battery wear-out.

Figure 22:
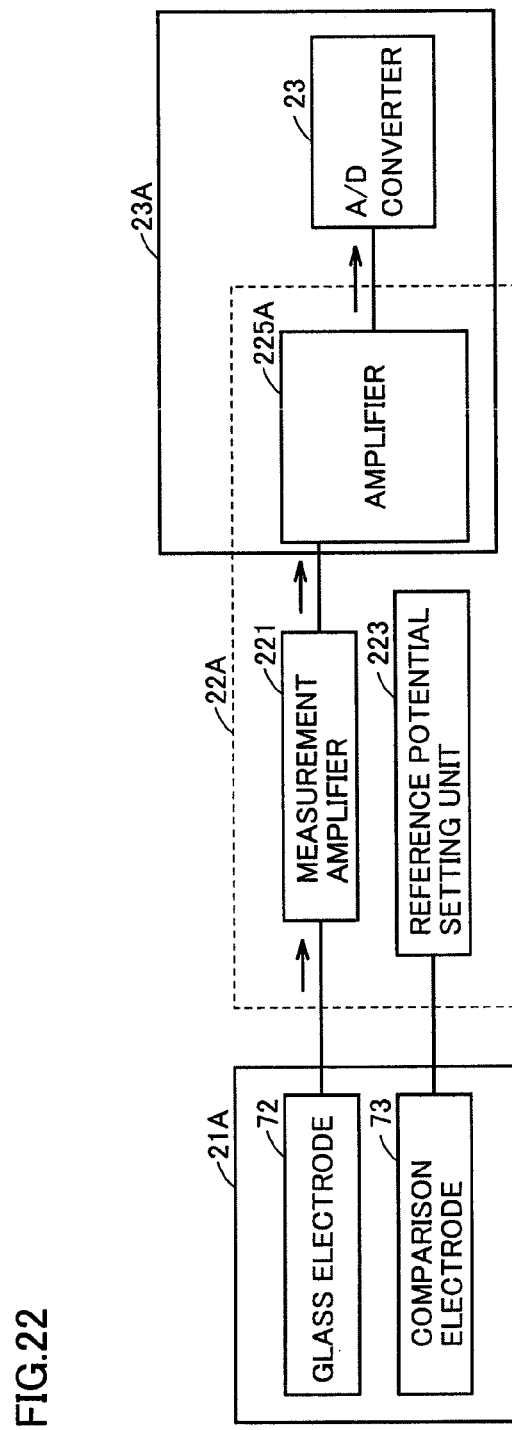
FIG. 22 is a functional block diagram of an amplifier circuit 22A in accordance with the second embodiment of the present invention.

FIG. 22 is a functional block diagram of an amplifier circuit 22A in accordance with the second embodiment of the present invention. Referring to FIGS. 21 and 22, amplifier circuit 22A is different from amplifier circuit 22 in that measurement amplifier 222 is omitted. Further, amplifier circuit 22A is different from amplifier circuit 22 in that it includes an amplifier 225A in place of differential amplifier 225. In module M shown in FIGS. 18 to 20, amplifier 225A and A/D converter 23 constitute A/D converting circuit 23A, and integrated as a module. Sensor unit 21A is different from sensor unit 21 in that ground electrode 83 is omitted.

In the second embodiment, comparison electrode 73 is connected to reference potential setting unit 223 and thereby the potential of comparison electrode 73 is fixed at the reference potential (specifically, 0V). As a result, in the second embodiment, the potential difference between the potential of glass electrode 72 and the reference potential is amplified by amplifier 225A.

Amplifier 225A amplifies only the output of measurement amplifier 221. Therefore, measurement amplifier 222 becomes unnecessary, and the power consumption by the amplifier circuit as a whole can be reduced. Thus, as shown in FIGS. 18 to 20, it becomes possible to operate detection device 20 with only one battery 32A.

In order to examine the performance of detection device 20 in accordance with the second embodiment, detection devices 20 were administered orally to three cows. Variation in measurement values transmitted from detection devices 20 retained in the rumens was examined. It was confirmed that after one month from the start of examination, the measurement values of detection devices 20 were stable.

On the other hand, when gel containing KCl solution was used as the internal solution in place of KCl saturated solution, the period in which the measurement values of detection devices were stable was about one to two weeks. The reason why the period in which the measurement values of detection devices were stable became shorter is considered that the concentration of internal buffer solution changed by the absorption of the measured sample into gel.

Further, battery duration was examined using a plurality of detection devices 20. The battery duration was 1.5 to 2 months.

The distance that ensures stable wireless communication between transmitter/receiver 4A and detection device 20 was about 20 m, and the farthest communication distance was 25 m. Wireless communication was determined to be stable if acknowledgement data was received by transmitter/receiver 4A.

As described above, in the second embodiment, KCl saturated solution is used as the internal solution of the pH sensor. Thus, the problem that measurement accuracy of rumen pH degrades as the detection device stays longer in the rumen can be prevented.

Further, according to the second embodiment, a command is transmitted from the transmitter/receiver to the detection device. In the monitoring system in accordance with the first embodiment, a setting unit is used for transmitting a command to the detection device. In the monitoring system in accordance with the second embodiment, various commands can be sent to the detection device without using the setting unit. Therefore, configuration of the monitoring system can be simplified.

Further, in the second embodiment, amplifier circuit 22A amplifies the output signal of sensor unit 21A in accordance with non-differential amplification method. Thus, power consumption of detection device 20 can be reduced.

It is naturally preferable that detection device 20 has longer operable time. From the viewpoint of milk production yield of milk cows, it is particularly important to manage the state inside the rumen in a specific period. The period is, preferably, a period of three to four months after delivery to the end of stage of lactation. The detection device in accordance with the embodiments of the present invention can continuously detect the state of rumen for the period that requires rumen management.

In the embodiments of the present invention, rumen acidosis has been described as a representative example of a change of internal state of the rumen. According to the present invention, it is also possible to detect rumen alkalosis. Rumen alkalosis refers to a state in which the value of rumen pH becomes high, as ammonia is generated excessively because of fermentation in the rumen.

In the embodiments of the present invention, pH value of rumen liquid is measured to detect the state in the rumen. It is noted, however, that the parameter to be measured is not limited to pH, and both pH and temperature may be measured.

Though a cow has been described as a ruminant in the embodiments of the present invention, the present invention is applicable to ruminants other than cows, such as sheep and goat, for detecting and monitoring the state of rumen. For a ruminant smaller in size than cows, the size of detection device should be made smaller than that described above. Further, the weight of detection device should also be made lighter than the values (120 to 150 g or 160 to 200 g) mentioned above.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

REFERENCE SIGNS LIST 1 cow, 2, 20 detection device, 2a housing, 2b housing body, 2c cap, 2d coupling portion, 2e opening, 2f, 2g screws, 3 rumen, 3a esophagus, 3b upper layer, 3c middle layer, 3d lower layer, 4 receiver, 4A transmitter/receiver, 5 LAN, 6 hub, 7 monitoring server, 8 web server, 9 WAN, 10 router, 11 information terminal, 11a, 12a personal computer, 11b portable terminal, 12 setting unit, 12b transmitter, 21, 21A sensor unit, 22, 22A amplifier circuit, 23 A/D converter, 24, 44 CPU, 25, 45 wireless module, 26, 26A, 46 antenna, 26a dielectric chip, 26b conductor, 27, 47 ROM, 28, 48 RAM, 29, 49 EEPROM, 30, 50 RTC, 31, 51 UART interface circuit, 32, 32A battery, 33 power source IC, 35 pH sensor, 36 temperature sensor, 41 USB interface circuit, 42 display unit, 43 operation unit, 45 wireless module, 46 antenna, 52 LAN interface circuit, 53 power source module, 61, 63 O-ring, 62 separating portion, 71 glass film, 72 glass electrode, 73 comparison electrode, 74 porous resin, 75 thermister, 76 internal buffer solution, 77 gel, 77A internal solution, 81 ground electrode, 82 battery holder, 83 connector, 84 inner case, 85 holder, 86 packing, 87 silicone filler, 88 rumen liquid, 90 recovery instrument, 91 wire, 92 magnet, 100 monitoring system, 120 setting unit, 201, 202 group of cows, 221, 222 measurement amplifier, 223 reference potential setting unit, 225 differential amplifier, 225A amplifier, C1 to C4 circuit board, M module.

The invention claimed is:

1. A detection device configured to detect internal state of a rumen of a ruminant, comprising
   a housing formed of a material having resistance to liquid component of contents in said rumen and having physical strength to withstand movement and inner pressure of said rumen, configured to enable oral administration to said ruminant and engageable with a recovery instrument orally inserted to the inside of said rumen;
   said housing having an opening on a side surface of said housing introducing said liquid component to a first chamber inside said housing, and said housing having a magnetic body provided at a first end of said housing and exposed to an outside, and said housing including a coupling portion formed of said magnetic body and formed to be detachable from a housing body;
   said detection device further comprising:
     a separating portion configured to section the inside of said housing to said first chamber and a second chamber not permitting entrance of said liquid component;
     a measuring unit placed in said first chamber of said housing and configured to measure a parameter related to said liquid component, said measuring unit including a pH sensor and said parameter including a pH value of said liquid component;

a storage unit placed in said second chamber of said housing configured to store information related to operational conditions of said detection device;

a control unit placed in said second chamber of said housing and configured to generate data related to said parameter from result of measurement by said measuring unit, based on said information stored in said storage unit;

a communication unit placed in said second chamber of said housing and configured to transmit through wireless communication said data related to said parameter generated by a process by said control unit; and a battery configured to supply electric power at least to said control unit and said communication unit.

2. The detection device according to claim 1, wherein said housing includes a tapered portion tapered to be gradually narrower toward a front edge; and a portion defining said second chamber of said housing is configured to allow opening and sealing.

3. The detection device according to claim 1, wherein said communication unit is configured to be capable of receiving through wireless communication new information updating at least part of said operational conditions of said detection device; and said control unit updates said information stored in said storage unit with said new information, when said new information is received by said communication unit.

4. The detection device according to claim 1, wherein said information stored in said storage unit includes a unique number of said detection device, and transmission schedule of said data related to said parameter.

5. The detection device according to claim 1, wherein said pH sensor includes a glass electrode, a gel containing internal solution, a comparison electrode at least partially arranged in said gel, a liquid junction formed of porous resin configured to control amount of liquid junction of said internal solution flowing out from said gel, and a temperature sensor configured to perform temperature compensation of pH measurement value of said liquid component by said glass electrode and said comparison electrode.

6. The detection device according to claim 5, wherein said detection device further includes an amplifier circuit configured to amplify an output of said pH sensor.

7. The detection device according to claim 1, wherein said pH sensor includes a glass electrode, a potassium chloride saturated solution as an internal solution, a comparison electrode at least partially immersed in said potassium chloride saturated solution, a liquid junction formed of porous resin for controlling amount of liquid junction of said internal solution, and a temperature sensor configured to perform temperature compensation of pH measurement value of said liquid component by said glass electrode and said comparison electrode.

8. The detection device according to claim 1, wherein said housing includes a cap, said cap being transparent to an electromagnetic wave and formed to be detachable and to seal an inner space of said cap, said cap being formed of a resin, and said cap having a tapered shape and provided at a second end of said housing.

9. A monitoring system, comprising:

a detection device configured to detect internal state of a rumen of a ruminant;

said detection device including a housing formed of a material having resistance to liquid component of contents in said rumen and having physical strength to withstand movement and inner pressure of said rumen, configured to enable oral administration to said ruminant and engageable with a recovery instrument orally inserted to the inside of said rumen;

said housing having an opening on a side surface of said housing introducing said liquid component to a first chamber inside said housing, and said housing having a magnetic body provided at a first end of said housing and exposed to an outside, and said housing including a coupling portion formed of said magnetic body and formed to be detachable from a housing body;

said detection device further including a separating portion configured to section the inside of said housing to said first chamber and a second chamber not permitting entrance of said liquid component;

a measuring unit placed in said first chamber of said housing and configured to measure a parameter related to said liquid component, said measuring unit including a pH sensor and said parameter including a pH value of said liquid component, a storage unit placed in said second chamber of said housing and configured to store information related to operational conditions of said detection device, a control unit placed in said second chamber of said housing and configured to generate data related to said parameter from result of measurement by said measuring unit, based on said information stored in said storage unit, a communication unit placed in said second chamber of said housing and configured to transmit through wireless communication said data related to said parameter generated by a process by said control unit, and a battery configured to supply electric power at least to said control unit and said communication unit;

said monitoring system further comprising:

a communication device configured to be capable of wireless communication with said detection device, and to receive said data transmitted through wireless communication from said detection device; and a monitoring device configured to collect said data received by said communication device and to monitor state of said rumen using said data.

10. The monitoring system according to claim 9, wherein said communication unit of said detection device includes a first antenna configured to transmit radio wave of transmission power of at most 10 mW;

said communication device includes a second antenna configured to receive said data through wireless communication; and said second antenna has higher gain than said first antenna.

11. The monitoring system according to claim 10, wherein said communication device is at least arranged at one location and capable of receiving said data transmitted from each of a plurality of detection devices; and said monitoring device collects data received by said communication device.

12. The monitoring system according to claim 9, wherein said communication unit of said detection device is configured to be capable of receiving through wireless communication new information updating at least part of said operational conditions of said detection device;

said control unit updates said information stored in said storage unit with said new information, when said new information is received by said communication unit; and said communication device includes
- a receiver configured to receive said data transmitted through wireless communication from said detection device and
- a setting unit configured to be capable of transmitting through wireless communication said new information corresponding to each of the plurality of detection devices.

13. A recovery method of recovering a detection device placed in a rumen of a ruminant and configured to detect inner state of said rumen, said detection device including
- a housing formed of a material having resistance to liquid component of contents in said rumen and having physical strength to withstand movement and inner pressure of said rumen, configured to enable oral administration to said ruminant and engageable with a recovery instrument orally inserted to the inside of said rumen;

said housing having a through hole on a side surface of said housing formed to introduce said liquid component to a first chamber inside said housing, said housing having a magnetic body provided at a first end of said housing and exposed to an outside, and said housing including a coupling portion formed of said magnetic body and formed to be detachable from a housing body;

said detection device further including
- a separating portion configured to section the inside of said housing to said first chamber and a second chamber not permitting entrance of said liquid component; and
- a measuring unit placed in said first chamber of said housing configured to measure a parameter related to said liquid component, said measuring unit including a pH sensor and said parameter including a pH value of said liquid component;

said recovery method comprising the steps of:
- inserting a recovery instrument having a portion engageable with said detection device retained in the body of said ruminant to said rumen;
- engaging said recovery instrument with said detection device; and
- recovering said recovery instrument and thereby taking out said detection device from the mouth of said ruminant.

* * * * *